United States Patent
Lee et al.

(10) Patent No.: US 11,065,469 B2
(45) Date of Patent: Jul. 20, 2021

(54) REGION DIVISION METHOD FOR LASER TREATMENT, AND LASER TREATMENT METHOD AND APPARATUS USING THE SAME

(71) Applicant: OH & LEE MEDICAL ROBOT, INC., Daejeon (KR)

(72) Inventors: Jung Ho Lee, Daejeon (KR); Jung Woo Heo, Daejeon (KR); Jeong Soo Lim, Daejeon (KR); Yong Soo Lee, Daejeon (KR)

(73) Assignee: OH & LEE MEDICAL ROBOT, INC, Daejeon (KR)

( * ) Notice: Subject to any disclaimer, the term of this patent is extended or adjusted under 35 U.S.C. 154(b) by 133 days.

(21) Appl. No.: 16/491,343

(22) PCT Filed: Mar. 5, 2018

(86) PCT No.: PCT/KR2018/002577
§ 371 (c)(1),
(2) Date: Sep. 5, 2019

(87) PCT Pub. No.: WO2018/164429
PCT Pub. Date: Sep. 13, 2018

(65) Prior Publication Data
US 2020/0023192 A1    Jan. 23, 2020

(30) Foreign Application Priority Data
Mar. 6, 2017   (KR) .................. 10-2017-0028042

(51) Int. Cl.
*A61N 5/06*   (2006.01)
*G06T 7/11*   (2017.01)
(Continued)

(52) U.S. Cl.
CPC .............. *A61N 5/0616* (2013.01); *G06T 7/11* (2017.01); *A61N 2005/067* (2013.01);
(Continued)

(58) Field of Classification Search
CPC ............ A61N 5/0616; A61N 2005/067; A61N 2005/105; A61N 5/103; G06T 7/11;
(Continued)

(56) References Cited

U.S. PATENT DOCUMENTS

2012/0314224 A1   12/2012   Luellau
2013/0204237 A1   8/2013    Fabrikant

FOREIGN PATENT DOCUMENTS

EP     2937033 A1     10/2015
JP     2016-064313 A   4/2016
(Continued)

*Primary Examiner* — Carl H Layno
*Assistant Examiner* — Aya Ziad Bakkar
(74) *Attorney, Agent, or Firm* — Novick, Kim & Lee, PLLC; Sang Ho Lee

(57) ABSTRACT

Provided is a region division method for laser treatment, and a laser treatment method and apparatus using the same. The region division method for laser treatment according to the present invention divides an area of an object to be treated by laser irradiation into a plurality of treatment regions and includes constructing a three-dimensional image of the object; using the three-dimensional image to obtain a normal vector for each of a plurality of points located on a surface of the object; dividing the points on the surface of the object into one or more groups based on a similarity between the obtained normal vectors; and generating a closed curve including at least some of points grouped into the same group to set a treatment region.

19 Claims, 35 Drawing Sheets

(51) Int. Cl.
*A61N 5/067* (2006.01)
*G06T 7/00* (2017.01)

(52) U.S. Cl.
CPC .......... *A61N 2005/0629* (2013.01); *A61N 2005/0633* (2013.01); *A61N 2005/0643* (2013.01); *G06T 7/0012* (2013.01); *G06T 2207/20101* (2013.01); *G06T 2207/30088* (2013.01); *G06T 2207/30201* (2013.01)

(58) Field of Classification Search
CPC . G06T 2207/20101; G06T 2207/30201; G06T 7/136; G06T 7/0012; A61B 2034/107; A61B 34/30; A61B 34/70; A61B 18/203; A61B 2018/20353; A61B 2018/00452; A61B 34/20; Y10T 74/20305
See application file for complete search history.

(56) References Cited

FOREIGN PATENT DOCUMENTS

| | | | | |
|---|---|---|---|---|
| KR | 10-0938378 B1 | 1/2010 | | |
| KR | 10-1015881 B1 | 2/2011 | | |
| KR | 101015881 B1 | * 2/2011 | ........... | A61B 18/203 |
| KR | 10-1522690 B1 | 5/2015 | | |
| KR | 10-2016-0122581 A | 10/2016 | | |
| WO | 2004/086947 A2 | 10/2004 | | |
| WO | 2008/001284 A2 | 1/2008 | | |

* cited by examiner (a)

(b)

REGION DIVISION METHOD FOR LASER TREATMENT, AND LASER TREATMENT METHOD AND APPARATUS USING THE SAME

TECHNICAL FIELD

The present invention relates to a method and an apparatus of irradiating a laser for treatment on a surface of an object such as human's face or skin.

BACKGROUND ART

Today, a variety of laser treatment methods by irradiating the laser beam on the skin have been developed to achieve the purpose of treatment, etc., and have been still actively studying a medical laser apparatus for use the laser treatment methods.

The treatment methods using the laser has been using for a variety of purposes such as to promote hair growth or prevent hair loss, skin peel, skin regeneration or skin whitening, or wrinkle, spot, stain, blemish and pigment removal, etc.

However, a user, such as a physician, manually operates the laser treatment apparatus to perform the treatment in the conventional art.

Accordingly, there is a problem that the reliability of the treatment may be decreased by lowering the accuracy of the treatment, and it may be difficult for a practitioner such as doctor to maintain concentration in long-term treatment as he is responsible for laser treatment and spends a lot of time.

DISCLOSURE

Technical Problem

An object of the present invention is to provide a region division method for laser treatment which can improve an effect of treatment by effectively irradiating a laser on an object having a curved profile such as face, and a laser treatment method and apparatus using the same.

Technical Solution

According to an embodiment of the present invention, a region division method for laser treatment divides an area of an object to be treated by laser irradiation into a plurality of treatment regions and comprises constructing a three-dimensional image of the object; using the three-dimensional image to obtain a normal vector for each of a plurality of points located on a surface of the object; dividing the points on the surface of the object into one or more groups based on a similarity between the obtained normal vectors; and generating a closed curve including at least some of points grouped into the same group to set a treatment region.

According to an embodiment of the present invention, a laser treatment method performs treatment by dividing an area of an object to be treated by laser irradiation into a plurality of treatment regions and comprises constructing a three-dimensional image of the object; using the three-dimensional image to obtain a normal vector for each of a plurality of points located on a surface of an object; dividing the points on the surface of the object into one or more groups based on a similarity between the obtained normal vectors; generating a closed curve including at least some of points grouped into the same group to set a treatment region; setting a guide path which passes through the treatment region; setting a plurality of laser irradiation points arranged on the guide path; and sequentially irradiating a laser to a position corresponding to each of the laser irradiation points in the surface of the object.

According to an embodiment of the present invention, a laser treatment apparatus performs treatment by dividing an area of an object to be treated by laser irradiation into a plurality of treatment regions and comprises a vision controlling unit for constituting a three-dimensional image of an object, and for setting a treatment region irradiated by a laser on a surface of the object, a guide path passing through the treatment region, and laser irradiation points arranged on the guide path; a laser unit for sequentially irradiating the laser to a position corresponding to the laser irradiation points in the surface of the object; and a motion controlling unit for controlling movement of the laser unit and laser irradiation based on the set guide path and the laser irradiation points; wherein the vision controlling unit is configured to use the three-dimensional image to obtain a normal vector for each of the plurality of points located on the surface of the object; divide the points on the surface of the object into one or more groups based on a similarity between the obtained normal vectors; and generate a closed curve including at least some of points grouped into the same group to set a treatment region.

On the other hand, said methods may be practiced in a computer-readable recording medium in which a computer-executable program is stored, or may be provided in the program itself.

In addition, the laser treatment apparatus may use a wired or wireless network such as the Internet may be controlled as described above in conjunction with an external server.

Advantageous Effects

According to an embodiment of the present invention, it will be obtained following effects that the precision and the stability of the laser treatment may be improved, the operating time required to perform the laser treatment by a practitioner such as doctor may be reduced, and long-term treatment may be effectively performed.

According to another embodiment of the present invention, by grouping points on a surface of an object according to a similarity between angles of normal vectors to generate a closed curve and divide an area of the object into a plurality of treatment regions for laser irradiation, vibration due to excessive movement of a laser treatment apparatus can be reduced.

In particular, when irradiating a laser using a robot arm with an end effector which serves to irradiate the laser, the movement of the end effector and the resulting vibration are reduced. Thus, the accuracy of laser irradiation can be further improved, and a patient can be treated in a more comfortable state.

According to further embodiment of the present invention, it may be possible to control the motion speed and the frequency inside and outside of a region of therapy, thereby more precisely controlling the positions of the laser irradiation point.

BEST MODE

Figure 1:
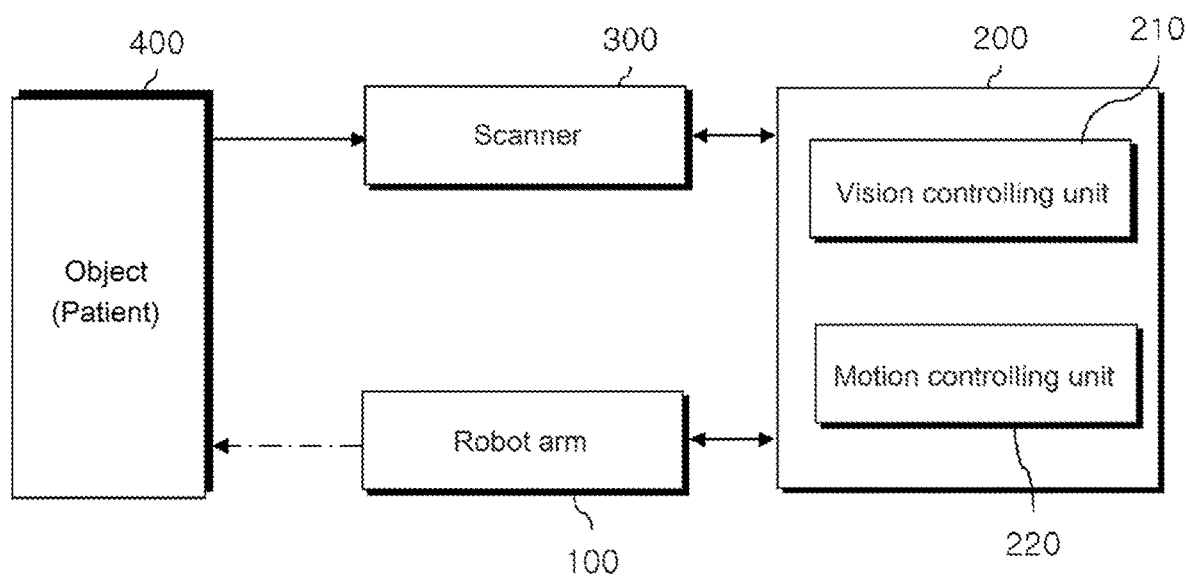
FIGS. 1 to 3 are block diagrams for explaining embodiments for the overall structure of a laser treatment apparatus according to the present invention.

A region division method for laser treatment of the present invention, and a laser treatment method and apparatus using the same will be described in detail with reference to the accompanying drawings.

The present invention may be modified in various ways and implemented by various exemplary embodiments, so that specific exemplary embodiments are illustrated in the drawings and will be described in detail below. However, it is to be understood that the present invention is not limited to the specific exemplary embodiments, but includes all modifications, equivalents, and substitutions included in the spirit and the scope of the present invention.

On the other hand, although the first and/or the terms of the second and so on in the present invention can be used in describing various elements, but the above elements shall not be restricted to the above terms. These terms are only to distinguish one component from other components, for example within that range departing from the scope of the concept of the present invention, a first element could be termed a second element. Similarly, the second component may be named as a first component.

As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, it will be understood that when an element is referred to as being "directly connected" or "directly coupled" to another element, there are no intervening elements present.

The terminology used herein is for the purpose of describing particular embodiments only and is not intended to be limiting of the invention. As used herein, the singular forms are intended to include the plural forms as well, unless the context clearly indicates otherwise.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, it is explained as an example that the laser is irradiated to the facial skin of the patient for ease of explanation, but the apparatus and the method according to the present invention can be applied whatever as long as irradiating the laser beam on the surface of a given object.

The accompanying drawings are intended to illustrate aspects of the present invention, but the scope of the present invention is not limited to this. In addition, the attached drawings will be noted that the portion or component is disposed is enlarged/reduced to better explain the characteristics of the present invention.

Hereinafter, a laser treatment apparatus using a robot arm and a method thereof according to the present invention is described in detail with reference to the accompanying drawings.

Figure 2:
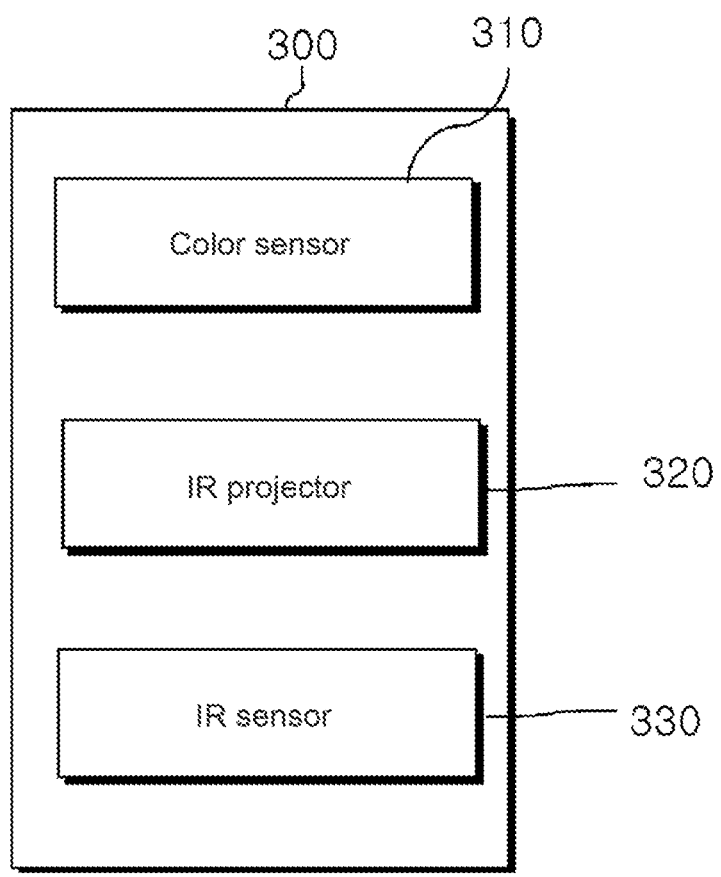
Figure 3:
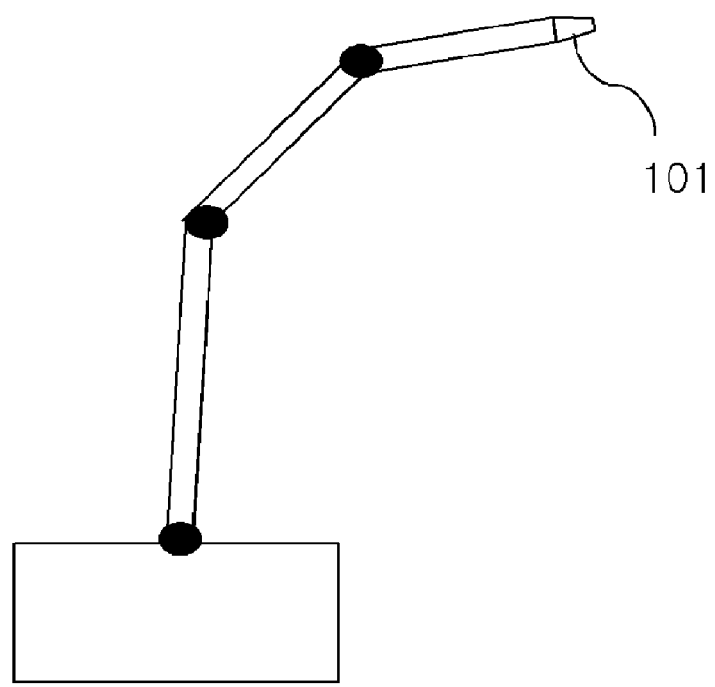

FIGS. 1 to 3 are block diagrams for explaining embodiments for the overall structure of the laser treatment apparatus according to the present invention.

Referring to FIG. 1, the laser treatment apparatus 10 may include a scanner 300, a robot arm 100, and a controlling unit 200.

The scanner 300 may collect raw data by scanning an object. Here, the raw data may include two-dimensional image and depth information.

The two-dimensional image may include color information, the diagnosis of the particular condition, such as telangiectasia may be possible according to the color information of a patient's skin. Further, the scanner may detect the size, location, or depth information, etc. for pores of the patient's face using the two-dimensional images and the depth information.

The scanner 300, as shown in FIG. 2, may include a color sensor 310 for photographing the two-dimensional color images, and an IR projector 320 and an IR sensor 330 for obtaining the three-dimensional depth data.

If the IR projector 320 may irradiate the IR light on the surface of an object 400, that is the surface of the patients' skin, the IR sensor 330 would obtain the depth data by detecting the IR light reflected from the surface of the object 400.

The color sensor 310 may obtain the two-dimensional color image by photographing the surface of the object.

The robot arm 100 may have an end-effector (EE) 101, as shown in FIG. 3, and irradiates the laser on the surface of the object 400 according to the control of the controlling unit 200. Specifically, the robot arm 100 may irradiate with the laser to the surface of the object 400 in response to a guide path (GP) through the end-effector 101. Such the robot arm 100 may be considered as a manipulator.

The controlling unit 200 may control the overall function and operation of the laser treatment apparatus 10.

The controlling unit 200 may include a vision controlling unit 210 and a motion controlling unit 220.

The vision controlling unit 210 may receive the raw data having the two-dimensional image and the depth information transmitted from the scanner 300, and configure the three-dimensional image of the object 400 on the basis of the raw data.

Here, the origin position of the raw data and the direction of the coordinates may vary depending on the object 400, for example, the shape and volume of the face, or various causes such as the scan starting point of the scanner 300, etc.

In addition, the vision controlling unit 210 may adjust the coordinates in alignment for the raw data. For this adjustment, the vision controlling unit 210 may detect the position of objects such as eyes, or a nose using face recognition algorithm, and obtain aligning homogeneous matrix.

The vision controlling unit 210 may set a region of interest (ROI) on the surface of the object 400 in the three-dimensional image.

The region of interest (ROI) may be a region including a portion that of requiring the laser irradiation, and set the region of interest (ROI) may be set by the user (e.g., physician), or may be automatically set by the three-dimensional image process.

For example, the user may set the region of interest (ROI) by clicking on the four corner points on the facial surface, and in this case, the normal vector corresponding to each of the corner point may be obtained.

The normal vector refers to a vector perpendicular to a curved surface of the object, for example face.

On the other hand, the vision controlling unit 210 may determine at least one of the color or the contrast of the surface of the object 400 based on the data transmitted form the scanner 300, and set the region of interest based on the determined result.

Specifically, the vision controlling unit 210 may detect a portion where the color or/and the contrast of the surface of the object 400 is (or are) different form the two-dimensional color image of the object 400 photographed by the scanner 300. In addition, the vision controlling unit may set the region of the interest to be included the other portion where the color and/or contrast is (or are) different than another portion.

More specifically, the reason for darkly appearing a specific portion is mainly due to the pigment of the depth or existence of the blood vessels, otherwise due to the shaded region by the contour of the skin.

Therefore, an algorithm may be applied to distinguish the regions which darkly appear due to the pigment or blood vessels of the face or darkly appear in the shade region due to the contour of the skin, and the dermatological treatment method, and the setting related to emission and irradiation of energy may be changed depending on this distinction.

For example, if the shaded region, caused by the contour of the skin, is occurred, it is caused by the skin stain or the atrophy of the subcutaneous fat layer due to skin aging, thereby treating firmness treatment, fac implants, fillers, and the like.

Further, when the shaded region caused by the scar is occurred, it may be necessary the scar treatment.

In the following, it may be referred to as a region of therapy (ROT) which is necessary for treatment by irradiating the laser on the surface of the object.

For example, the region of therapy (ROT) may be liver spots, freckles, burn marks, tattoos, acne, dark circles, scars, and the like, those are occurred in the human skin, the present invention is not limited to this, and it may be treatable regions by irradiating the laser of various kinds of wavelength or frequency.

The vision controlling unit 210 may determine this portion where color and/or contrast are different surroundings as the region of therapy (ROT).

According to an embodiment of the present invention, the region of interest (ROI) and the region of therapy (ROT) may be set separately as described above, but may be set only the region of therapy (ROT) which is actually irradiated as needed.

The vision controlling unit 210 constitutes a motion pattern on the object for the laser treatment on the basis of the determined (or set) information as described above, and the motion pattern may be configured by setting the guide path (GP) passing through the region of interest (ROI) or the region of therapy (ROT).

Then, the vision controlling unit 210 sets a plurality of points arranged on the guide path (GP). The plurality of points may represent the position where the laser is irradiated on the surface of the object, and the point on the guide path (GP) displayed on the two-dimensional image may be projected on the three-dimensional image.

In addition, the vision controlling unit 210 obtains the actual laser irradiation points to be irradiated on the surface of the object by selecting only those points positioned within the region of therapy (ROT) of the plurality of points arranged on the guide path (GP).

The motion controlling unit 220 controls the operation of the robot arm 100 on the basis of the information obtained by the vision controlling unit 210, while the end-effector 101 irradiates the laser as closely moving to the surface of the object.

Here, the interval between the surface of both the end-effector 101 and the surface of the object during the laser irradiation are preferably and constantly maintained during the movement, the interval may be set based on a focal distance of the laser.

For example, the motion controlling unit 220 may control the movement and the laser irradiation of the robot arm 100 on the basis of the guide path (GP) and the laser irradiation points set in the vision controlling unit 210.

In addition, the motion controlling unit 220 may emergently stop the laser irradiation by urgently stopping the robot arm 100, for example, the operation of the robot arm 100 may be stopped by the action or the voice of the doctor or the patient.

The laser treatment apparatus 10 according to the present invention may each operate in a manual mode or an automatic mode.

For example, in the automatic mode, the scanner 300 scans the surface of the object 400 to obtain the information about the surface of the object 400, and the controlling unit 200 may irradiate with the laser on the surface of the object 400 by controlling the robotic arm 100 on basis of the obtained information.

On the other hand, in the manual mode, the user such as a doctor has the controlling authorization, the robot arm 100 is operated by the control of the user.

The laser irradiation method using the laser treatment apparatus 10 according to the present invention will be described in detail with reference to the accompanying drawings.

FIGS. 4 to 19 are views for explaining the operation of the laser treatment apparatus according to embodiments of the present invention, the same explanation as explained with reference to FIGS. 1-3 of the operation and the construction of the laser treatment apparatus 10 will be omitted below.

Figure 4:
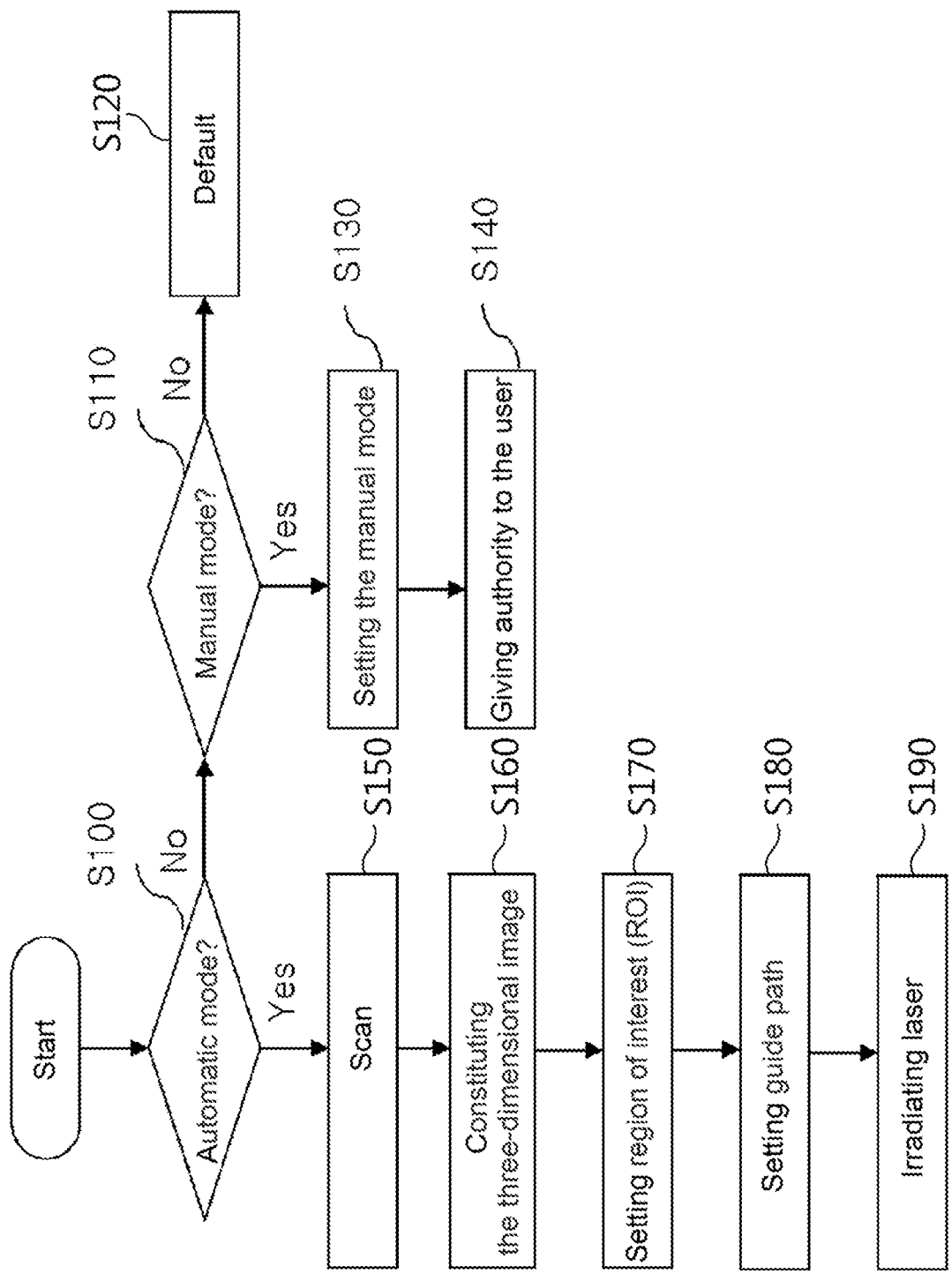
FIGS. 4 to 19 are views for explaining the operation of a laser treatment apparatus according to embodiments of the present invention.

Referring to FIG. 4, the controlling unit determines whether the current setting mode is the automatic mode or not or not (step S100). If the automatic mode is not, the controlling unit determines whether the current setting mode is the manual mode or not (S110).

For example, the user may set by selecting one of the manual mode or the automatic mode using a button mounted in the laser treatment apparatus 10 or a user interface (UI) provided in a touch screen.

It is determined that if the current setting mode is not the manual mode in the step S110, it is performed a different function previously predetermined (for example, Default setting) (S120).

On the other hand, if the current setting mode is the manual mode, it is determined that the setting status of the manual mode (S130), the controlling authorization is given to the user (S140).

Here, the operation of giving the controlling authorization to the user means that the controlling unit 200 may judge for themselves and limit the operation of the robot arm 100.

In the manual mode, the user may operate the robotic arm 100 on their own while performing the laser treatment.

In addition, in the semi-auto mode or the RAMI (Robot Assisted Manual Irradiation) mode, when the user moves a procedure point using a finger, a mouse, a pen mouse, a pen, etc. on the screen on which the object 400 is displayed, the robot arm (100) may perform laser treatment while moving the laser irradiation point accordingly.

On the other hand, it is determined that the current setting mode is the automatic mode in the step S100, the scanner 300 scans the surface of the object 400 according to the control of the controller 200 (S150). As a result of the scanning by the scanner 300, the raw data including the two-dimensional image and the depth information may be generated.

Then, the vision controlling unit 210 constitutes the three-dimensional image on the basis of the raw data obtained from the scanner 300 (S160).

For example, the canner may scan a plaster cast of a head shape of a person, as shown FIG. 5(A), it may be constituted the three-dimensional image as shown FIG. 5(B).

Hereinafter, for convenience of explanation, it will be described where the plaster cast of the head shape is regarded as the object 400.

After constituting the three-dimensional image, the region of interest (ROI) is set on the surface of the object 400 in the three-dimensional image (S170).

Figure 5:
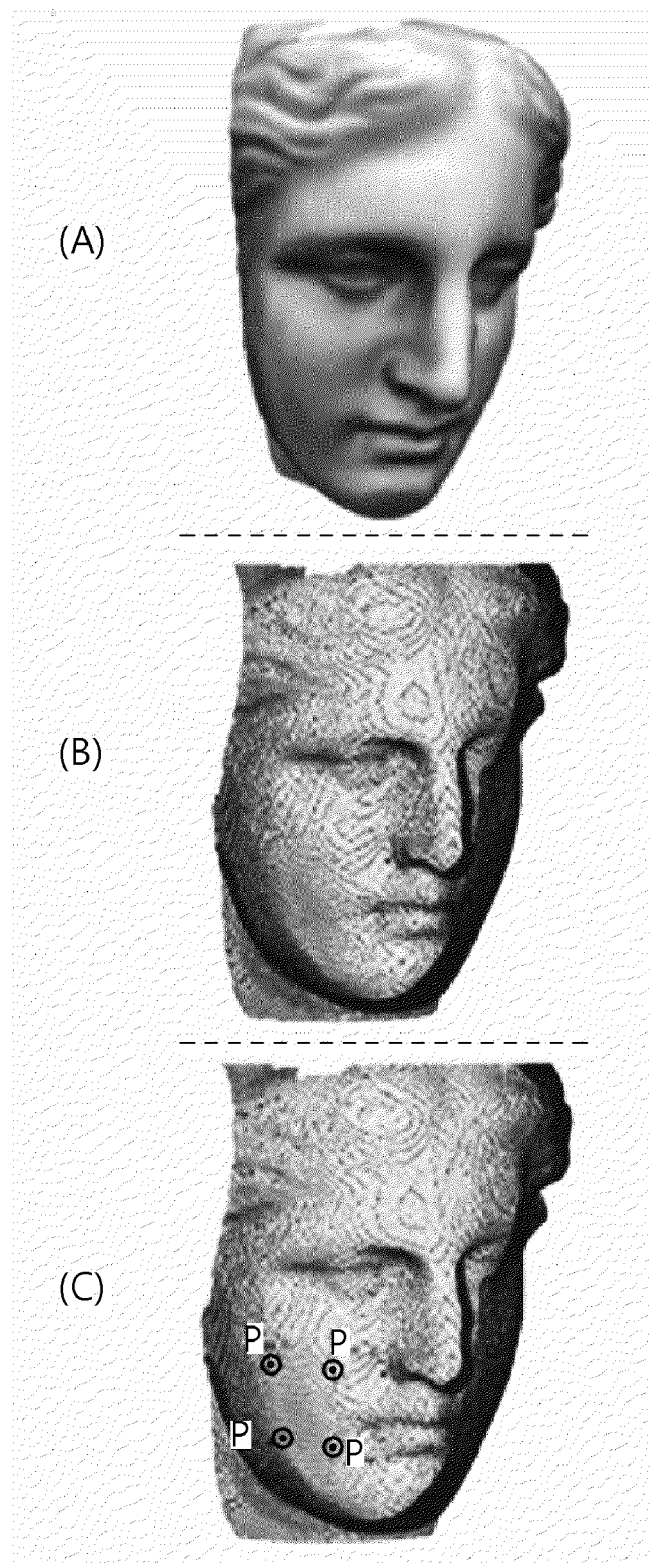

For example, the first corner point (Pcor, 1), the second corner point (Pcor, two), the third corner point (Pcor, 3), and the fourth corner point (Pcor, 4) may be set on the surface of the object 400 in the three-dimensional image, as shown in FIG. 5 (C). Then, the region of interest (ROI) may be set with a region partitioned by the vertices with four corner points such as the first, the second, the third and the four corner points.

In this embodiment, the region of interest (ROI) is set using the four corner points, but the number of corner points to be used the conditions may be changed. For example, it is possible to set the region of interest (ROI) by using at least three corner points.

Hereinafter, the first corner point (Pcor, 1), the second corner point (Pcor, two), the third corner point (Pcor, 3), and the fourth corner point (Pcor, 4) may be referred as the first point (P1), the second point (P2), the third point (P3), and the fourth point (P4), respectively.

Then, the guide path (GP) passing through the region of interest (ROI) may be set (step S180).

Figure 6:
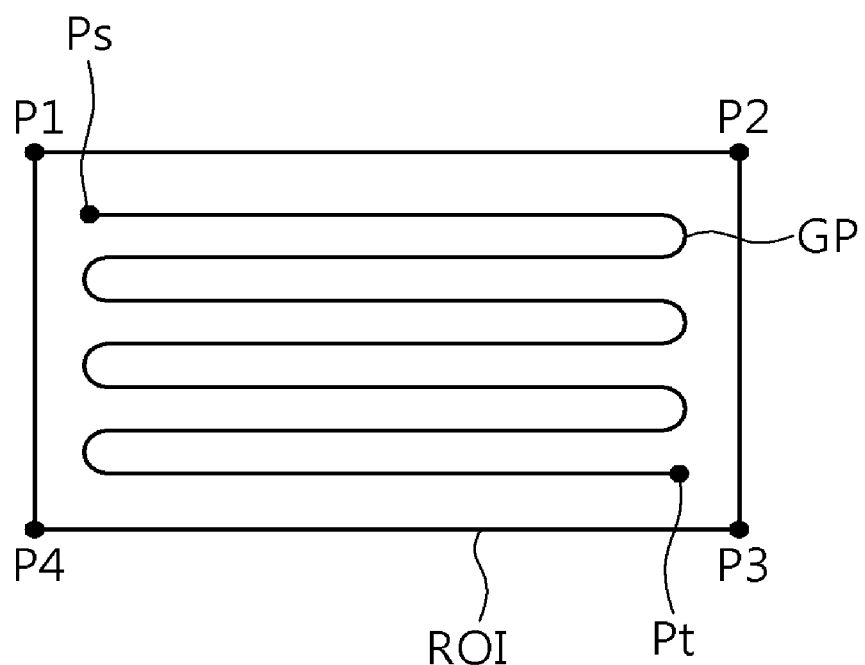

For example, as illustrated in FIG. 6, it is possible to set the guide path (GP) within the region of interest (ROI).

The starting point of the guide path (GP), i.e. the point at which the laser irradiation is started, is expressed as Ps, while the end point of the guide path (GP), i.e. the point at which the laser irradiation is ended, is expressed as Pt.

Then, the laser is irradiated in sequence to the laser irradiation points on the surface of the object corresponding to the guide path (GP) (Step S190).

The guide path (GP) may include a path where the robot arm 100 is irradiated with the laser. In other words, the robot arm 100 may irradiate with the laser to the surface of the object as moving in response to the guide path (GP).

The guide path (GP) may be regarded as including a path connecting the hitting point of the laser.

On the other hand, the regions of interest (ROI) may be set based on at least one a color, contrast, contour, texture and skin thickness of the surface of the object 400. It will be explained with reference to FIG. 7 as follows.

Figure 7:
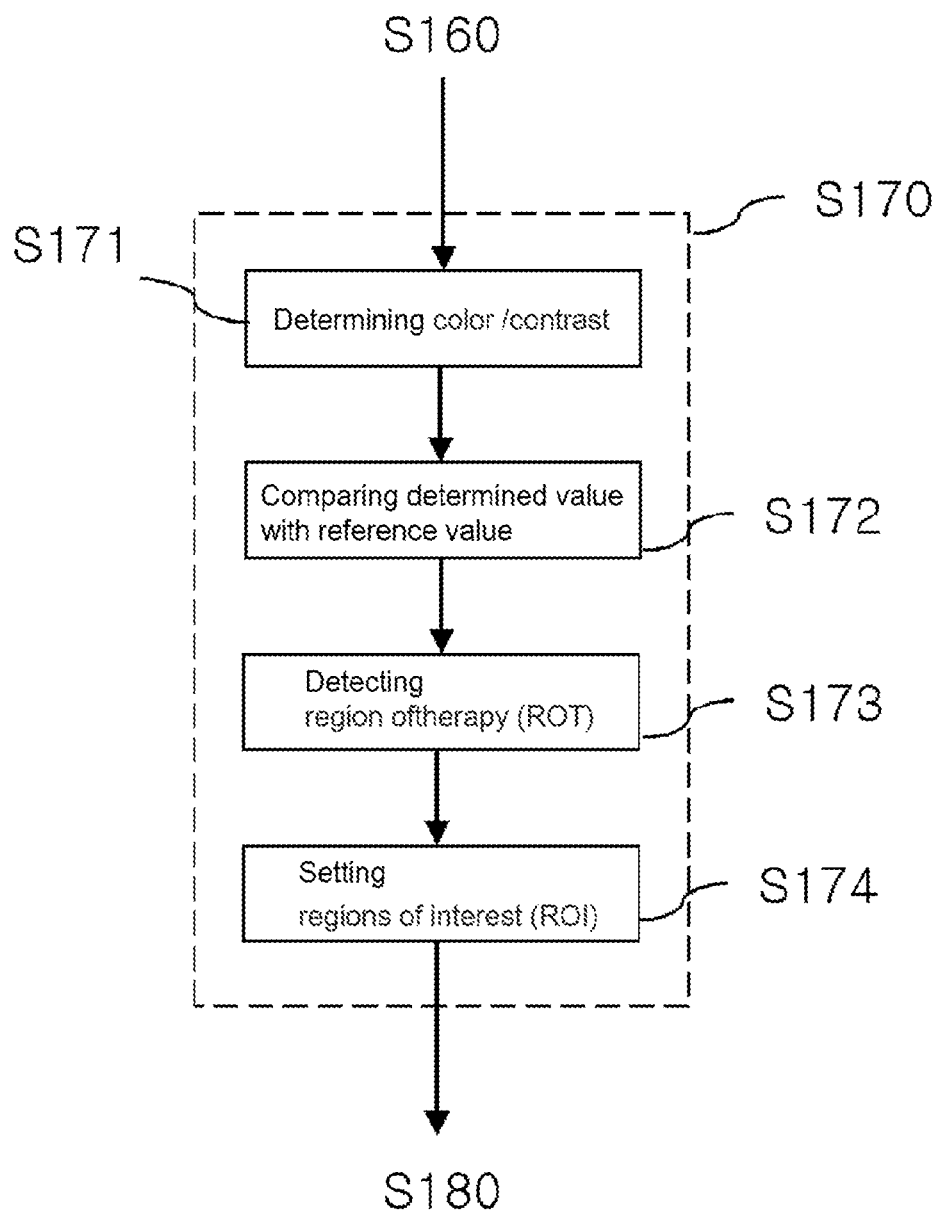

Referring to FIG. 7, in S170 step of setting the region of interest (ROI), the color and/or contrast of the surface of the object 400 is firstly determined (step S171). Here, the color and/or contrast of the surface of the object 400 may be determined from the two-dimensional color image of the object 400.

Since, the determined value is compared with the reference value (S172 step), the region of therapy (ROT), which is different surroundings at least one of color or contrast, is detected from the surface of the object 400 according to the comparison result (step S173).

For example, a region of normal (RON) and the region of therapy (ROT) may be distinguished on the basis of at least one of a color, contrast, contour and texture on the surface of the object 400.

Figure 8:
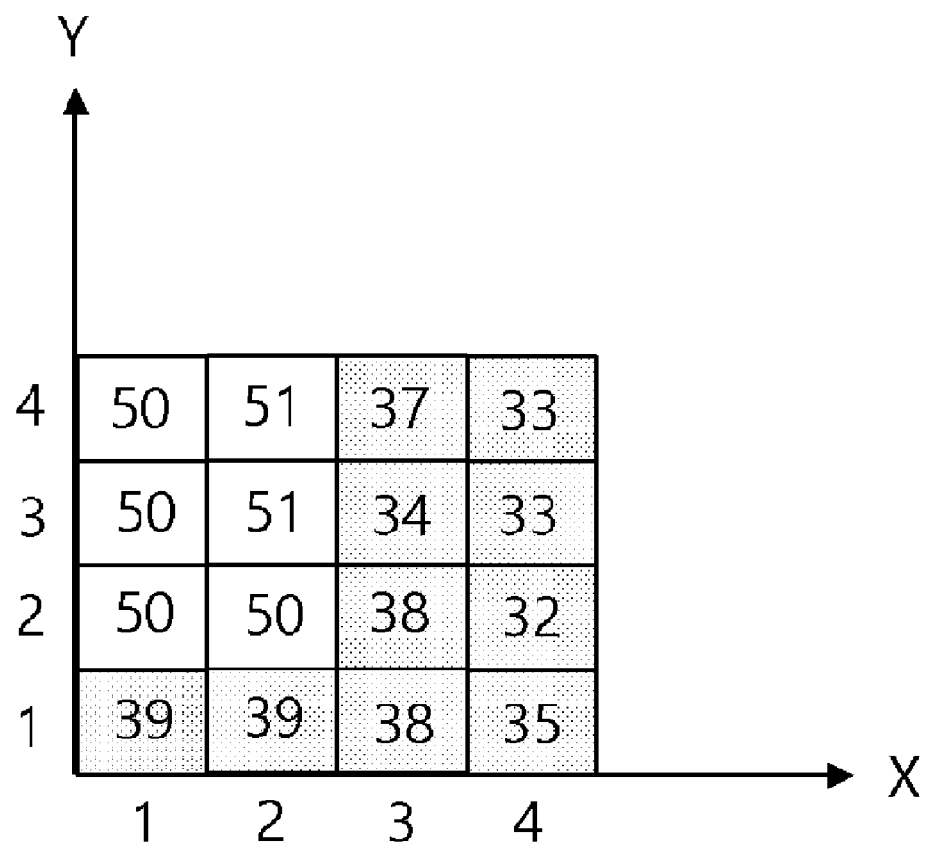

As shown in FIG. 8, when the total 16 of unit areas are arranged in 4×4 matrix form, the number expressed on each of the unit area may indicate the brightness value.

Here, it is assumed that the brightness value is 40, it is determined the region of therapy (ROT) with unit areas of (1, 1), (2, 1), (3, 1), (3, 2), (3, 3),(3, 4),(4, 1), (4, 2), (4, 3) and (4, 4) that the brightness value is smaller than 40, and the remained portion may be determined as the region of normal (RON).

The brightness of the region of therapy (ROT) may appear relatively darker than other portion, that is lower than the brightness of the region of normal (RON). Similarly, the color of the region of therapy (ROT) may appear relatively thicker than the color of the region of normal (RON). The thicker color means more darker than surroundings.

As such, the brightness value of the region of therapy (ROT) may be a lower portion than a predetermined reference brightness value. The reference brightness value may be varied in various ways depending on the surface state or characteristics (for example, contour or texture, etc.) of the object 400 or other factors such as the color tone.

Here, the reference brightness value may be a constant, but preferably may be set differently for each patient or treatment region. For example, the reference brightness value may be varied by considering a brightness value of the surrounding region to coincide the skin tone with a region adjacent to the region of therapy (ROT).

If the face of White is bright as a whole, the reference brightness value may be set relatively high based on the brightness value. The reason is that if the face is appeared with bright white as a whole, a portion requiring the treatment such as dots, spots required, i.e. the region of therapy, is more prominently appeared.

On the other hand, if the face is Mongoloid appeared relatively dark as a whole than Whites, the reference brightness value may be set relatively low compared with the brightness value of Whites.

In the above, an embodiment of the present invention has been described by the example of detecting the treatment region ROT according to the brightness value, but the present invention is not limited thereto, and the treatment region ROT may be detected according to the color value (for example, each of RBG three primary colors or ratio of RGE three primary colors, etc.).

After detecting the region of therapy (ROT), then the regions of interest (ROI) is set (S174).

As described above, the region of interest (ROI) includes the region of therapy (ROT), the region of interest (ROI) and the region of therapy (ROT) may be equally set.

As illustrated in FIG. 9(A), it is assumed that the region of therapy (ROT), where brightness, color, contour, and texture, etc. are different within the region of normal RON, is included on a predetermined region (R1) of the surface of the object 400, the form of the region of therapy (ROT) is arbitrarily set for convenience of the description and the present invention is not limited thereto.

In this case, as illustrated in FIG. 9(B), it may be set the first, second, third, and fourth points (P1, P2, P3, and P4) to be contacted the first line (L1) connecting the first point (P1) and the second point (P2) with the region of therapy (ROT), the second line (L2) connecting the second point (P2) and the third point (P3) with the region of therapy (ROT), the third line (L3) connecting the third point (P3) and the fourth point (P4) with the region of therapy (ROT), and the fourth line (L4) connecting the fourth point (P4) and the first point (P1) with the region of therapy (ROT).

In addition, regions divided with the first, the second, the third, and the fourth points (P1, P2, P3, and P4) may be set as the region of interest (ROI).

Here, the region of therapy (ROT) may be also included inside of the region of normal (RON), the region of interest (ROI) may include one portion of the region of normal (RON) as well as the region of therapy (ROT).

Hereinafter, it is assumed that a portion included within the region of interest (ROI) in the region of normal (RON) is a second region of normal (RON2) and the other portion does not include within the region of interest (ROI) in the region of normal (RON) is a first region of normal (RON1).

Figure 9:
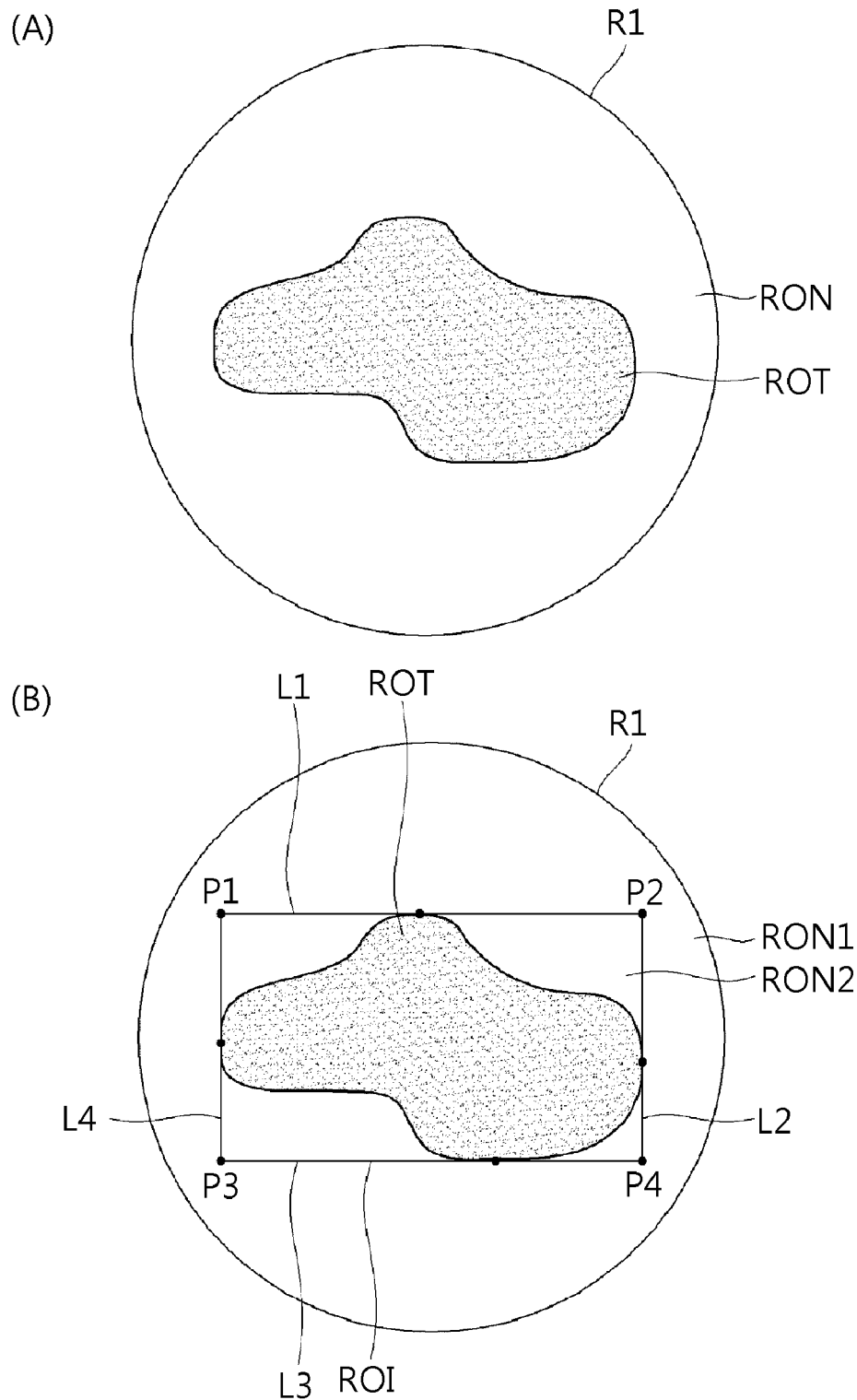

In the case of FIG. 9, as setting the region of interest (ROI), it is described only one case that a line connecting two near points is contacted on the region of therapy (ROT), the present invention may not be limited thereto.

Figure 10:
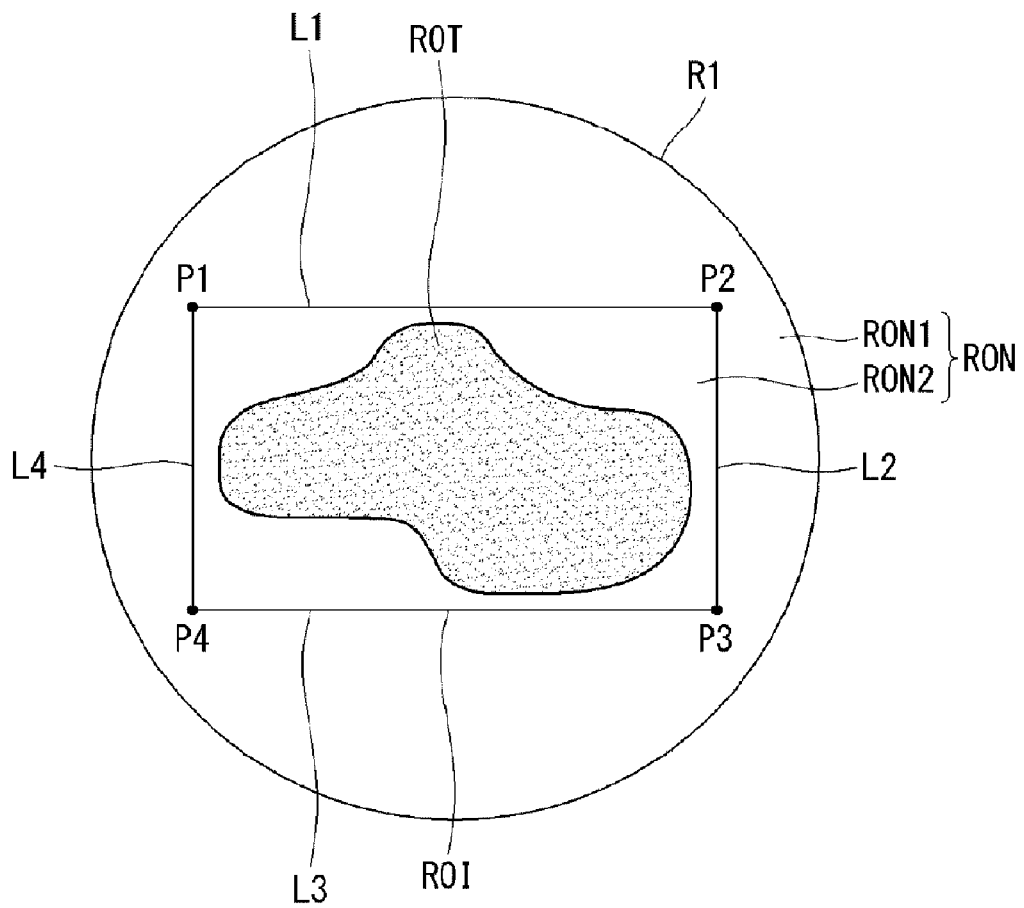

For example, as in a case of FIG. 10, at least one of lines (L1, L2, L3, and L4) connecting two near points is (or are) not in contact with the region of therapy (ROT).

Here, the number of lines connecting the points may be equal to or more than 5 lines.

Thus, the method of setting the region of interest (ROI) may be changed in various ways.

In case that the shape of the region of therapy (ROT) is the polygonal shape, it may be occurred that the region of therapy (ROT) and the region of interest (ROI) are same depending on the set position of the point.

On the other hand, the guide path (GP) is capable of being set within the region of therapy (ROT).

Figure 11:
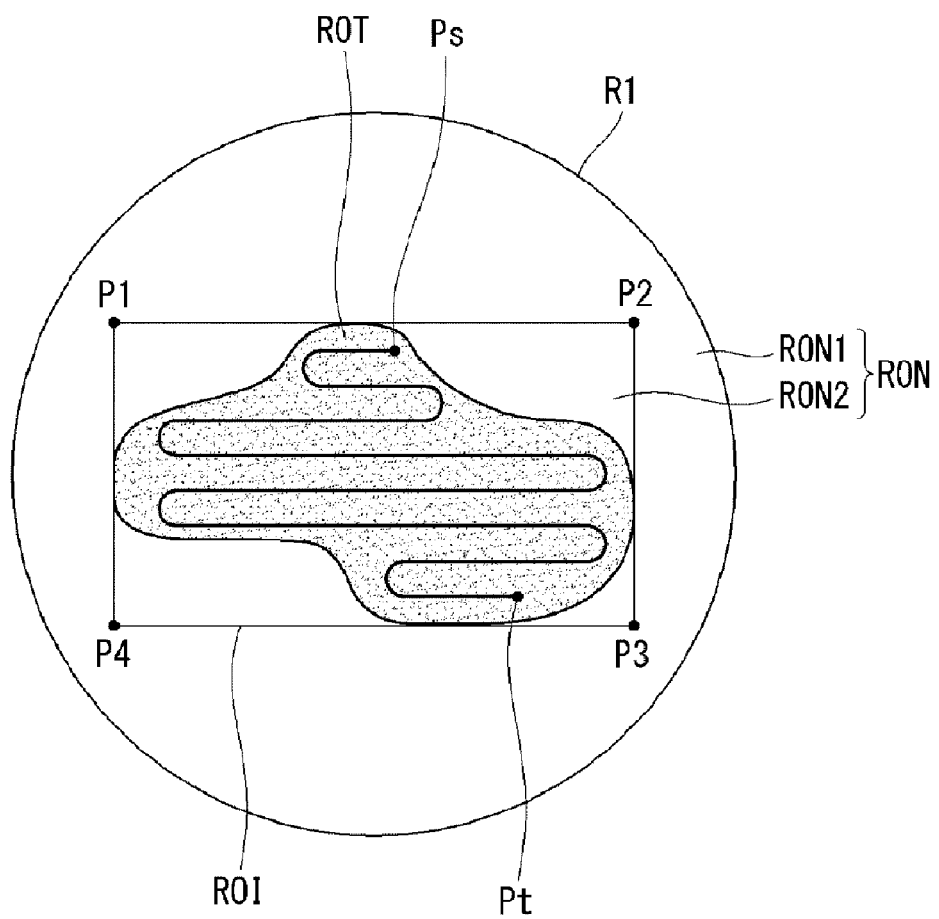
Figure 12:
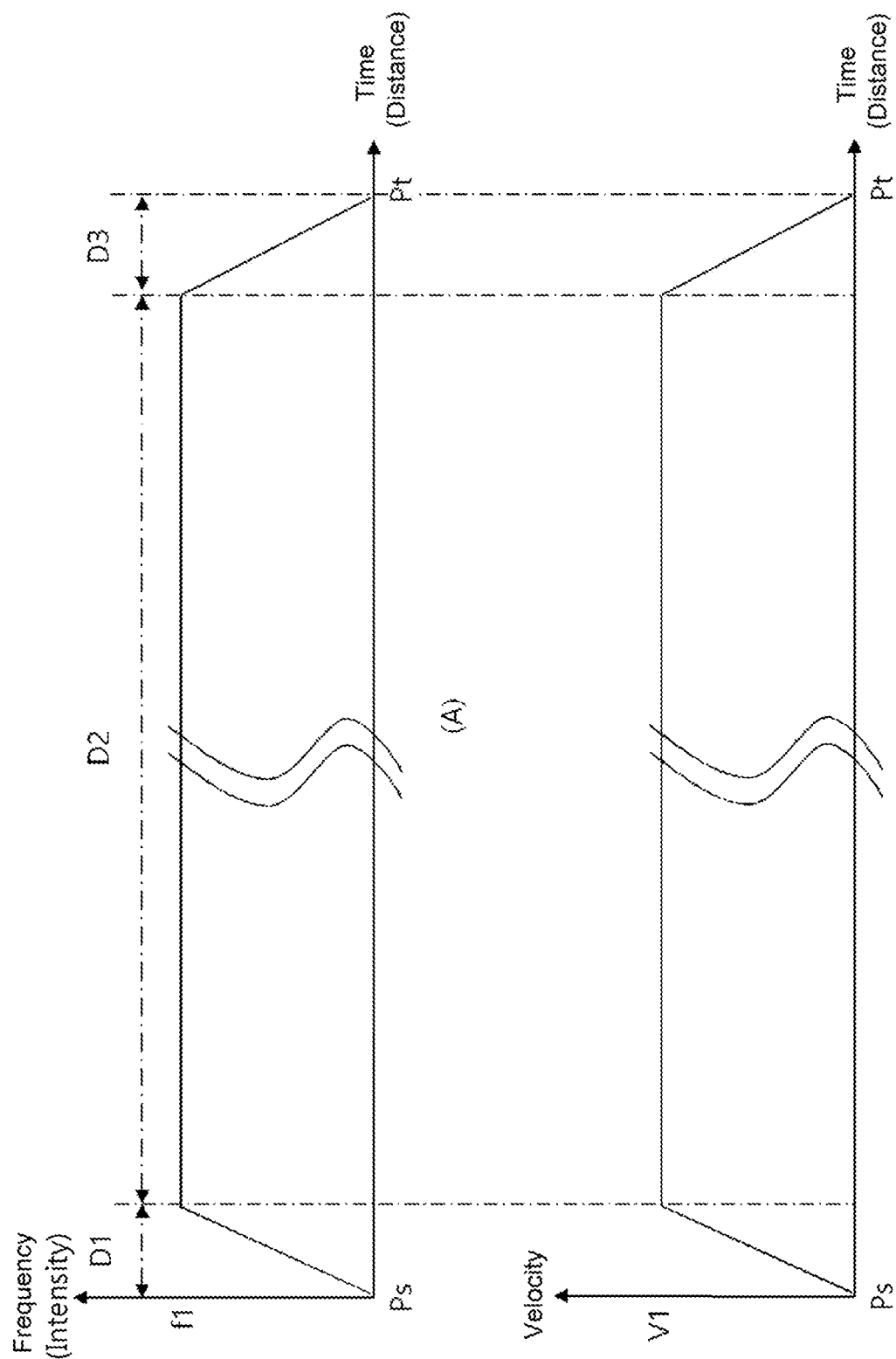
Figure 13:
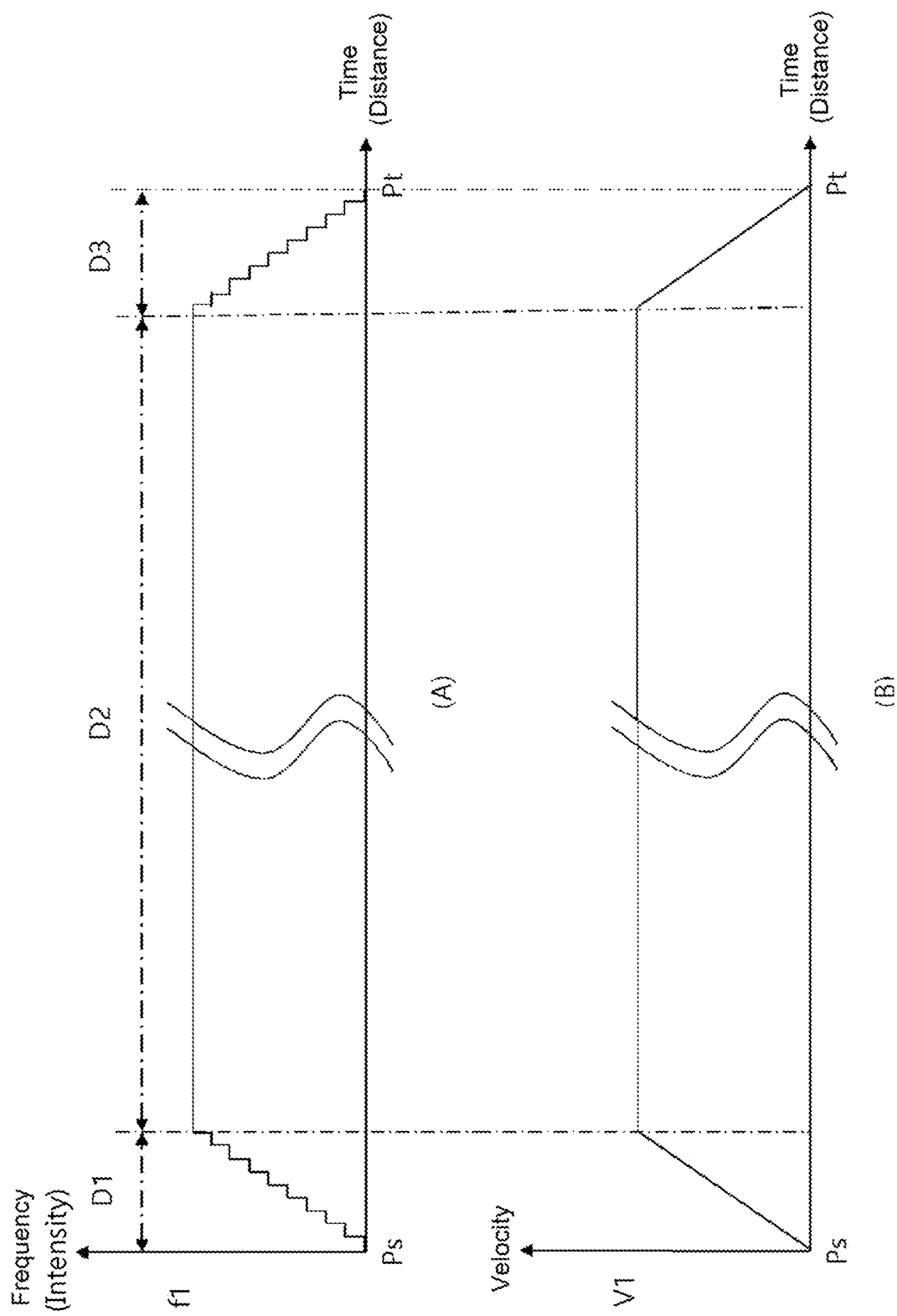

For example, it is possible to set the guide path (GP) with the zigzag form within the region of therapy (ROT), as shown in FIG. 11.

As such, the guide path (GP) is passing through the region of therapy (ROT), the laser is capable of being irradiated in the region of therapy (ROT).

On the other hand, it is possible to control the intensity (strength) and/or frequency of the laser in the beginning step and the end step of the laser irradiation, as further described below.

Referring to FIG. 12(A), at least one of the intensity (strength) or frequency of the laser is gradually raised in the beginning step of irradiating the laser, while at least one of the intensity or frequency of the laser is gradually decreased in the end step of the irradiating the laser.

In the following description, the beginning step of the laser irradiation is referred to an acceleration section (D1), while the end step of the laser irradiation is referred to a reduction section (D3).

As shown in FIG. 12(B), the moving speed of the robot arm 100 may be increased in the acceleration section (D1). That is, the movement speed of the robot arm 100 may be accelerated.

The occurrence reason of the acceleration section (D1) is because it takes some time from the time of supplying the power operating the robot arm 100 to the motor to the time of reaching the desired rotation speed.

In addition, in the deceleration section (D3), the moving speed of the robot arm 100 may be reduced. The reason why the deceleration section D3 is generated is that it takes some time from the time of shutting out the power supply to the motor operating the robot arm 100 to the stop of the motor similarly to the acceleration section D1.

In this way, when the intensity and/or frequency of the laser is gradually risen in acceleration section (D1) and is gradually decreased in the deceleration section (D3), it may be possible to uniformly irradiate the laser.

On the other hand, by varying the intensity and/or frequency of the laser for each section as described above, it is possible to irradiate the laser to the desired uniformity, to irradiate the laser on the desired region more strongly or weaker, or to reduce or increase the overlap rate of laser irradiation.

The intensity and/or frequency of the laser may be substantially proportional to the moving speed of the robot arm 100.

At this time, a maintain section (D2) may be occurred between the acceleration section (D1) and the deceleration section (D3), the intensity and/or frequency may substantially and constantly be maintained in the maintain section (D2) if the laser irradiation is not stopped.

The speed of the robot arm 100 may be substantially and constantly maintained in the maintain section (D2), for example, the speed of the arm 100 may be constantly maintained, or may be adjusted as desired during the section (D2) from the time at which the acceleration of the robot arm 100 is ended to the time at which the deceleration is started.

As shown in FIG. 13(A), it may be possible that of increasing with step curve the intensity and/or frequency of the laser in the acceleration section (D1) or decreasing in the deceleration section (D3).

In this case, it may be considered to gradually raise the intensity and/or frequency of the laser in the acceleration section (D1), and gradually decrease the intensity and/or frequency of the laser in the deceleration section (D3).

On the other hand, the guide path (GP) may be possible to deviate outside the region of therapy (ROT) within the region of interest (ROI).

Figure 14:
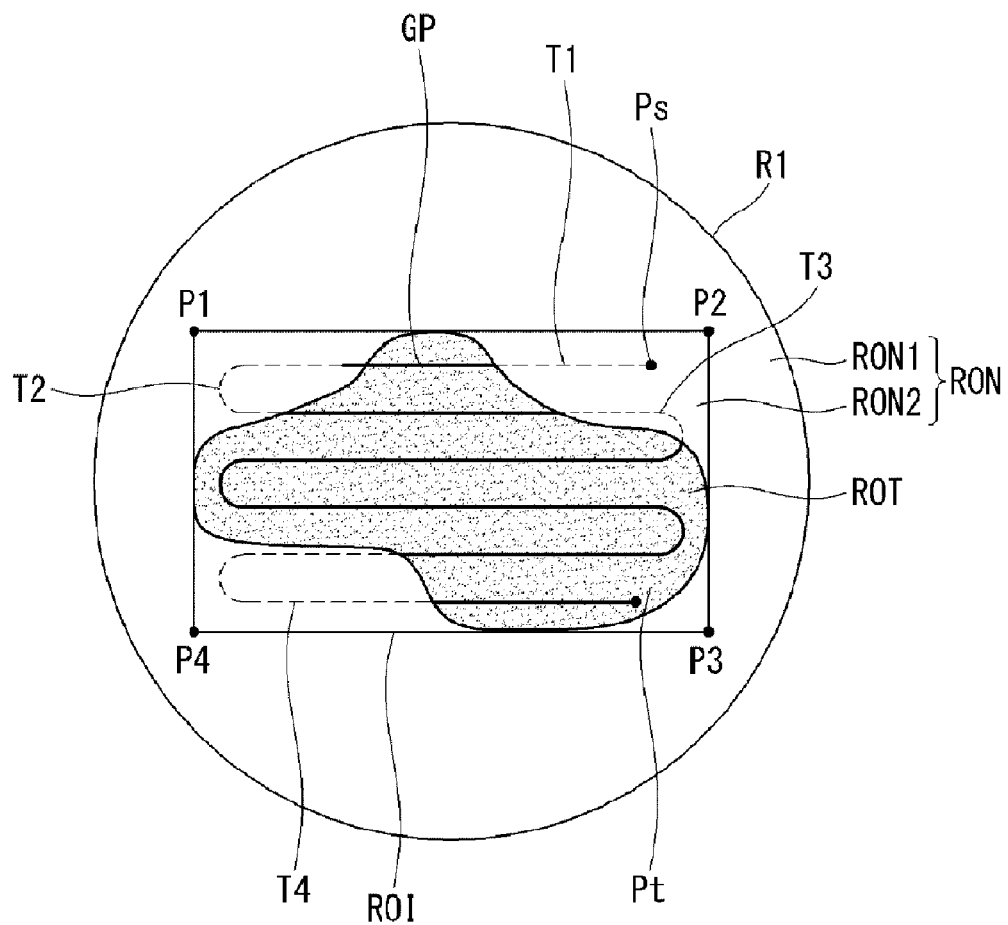

For example, as shown in FIG. 14 when the region of interest (ROI) include the region of therapy (ROT) and the region of normal, i.e., the second region of normal (RON2), the guide path (GP) may be passed all regions of the region of therapy (ROT) and the second region of normal (RON2).

In this case, the robot arm for irradiating the laser is turned on in correspondence to the region of therapy (ROT) or turned off in correspondence with the second region of normal (RON2).

Thus, it is possible to set the guide path (GP) without the relationship of the shape of the region of therapy (ROT) within the region of interest (ROI).

Further, the guide path (GP) includes a portion passing through the region of therapy (ROT) and the other portions (T1, T2, T3, and T4) passing through the region of normal (RON2) deviating outside the region of therapy (ROT).

Figure 15:
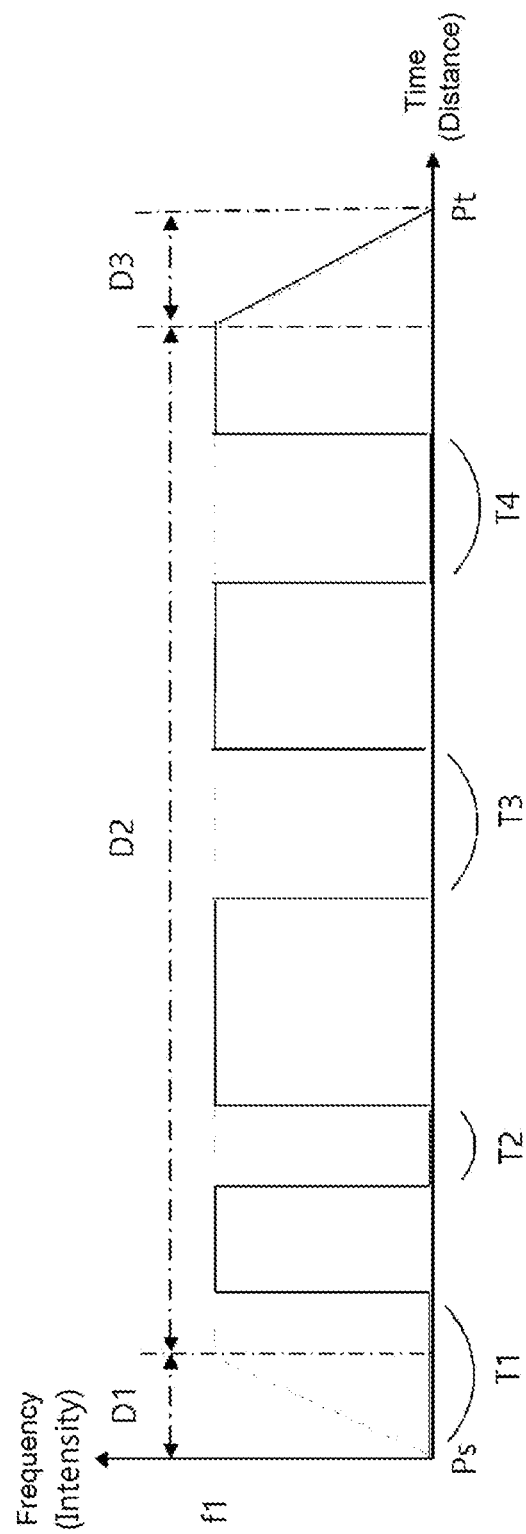

As shown in FIG. 15, the robot arm 100 may turn off the laser irradiation corresponding to the portion passing through the second region of normal (RON2) in the guide path (GP). In other words, it is considered that the robot arm 100 may turn on/off the laser irradiation depending on values output from the vision controlling unit such as color, brightness, ratio of RGB three primary colors, height, thickness of the surface of the object 400 in the course of irradiating the laser along the guide path (GP).

That is, the robot arm 100 moves corresponding to the guide path (GP) and may turn on the laser irradiation corresponding to the portion, where the color is appeared more darker or the brightness is lower than the surroundings, that is the region of therapy (ROT) and turn off the laser irradiation corresponding to the portion, where the color is appeared more lighter or the brightness is higher than the surroundings, that is the region of normal (RON).

Referring to FIG. 15, it may be known that the laser frequency and/or intensity is set substantially zero in the portions (T1, T2, T3, and T4) where the robot arm 100 is passing through the second region of normal (RON2).

In this case, the movement of the robot arm is possible to maintain substantially and constantly, thereby improving the accuracy of the treatment.

On the other hand, it is possible to adjust at least one of the frequency, the irradiation time, the number of the laser irradiation, the intensity of the laser depending on values output from the vision controlling unit such as color, brightness, ratio of RGB three primary colors, height, thickness of the region of therapy (ROT) under the control of the motion controlling unit 220.

Figure 16:
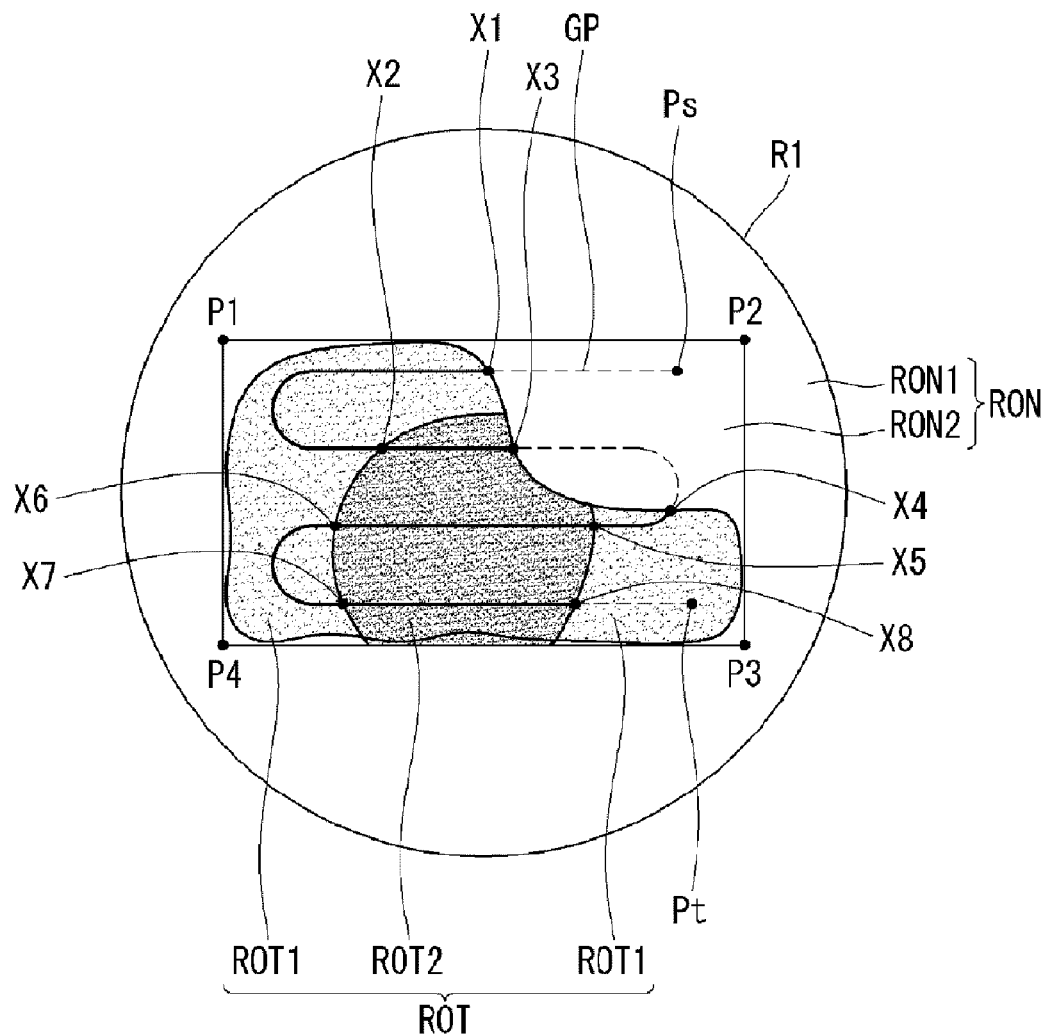

Referring to FIG. 16, the region of therapy (ROT) may include the first region of therapy (ROT1) and the second region of therapy (ROT2).

Here, the color of the second region of therapy (ROT2) may be darker than the first region of therapy (ROT1), or the brightness of the second region of therapy (ROT2) may be lower than the brightness of the first region of therapy (ROT1).

Alternatively, the brightness of the second region of therapy (ROT2) may be lower than the critical brightness value predetermined in advance, while the brightness of the first region of therapy (ROT1) may be higher than the critical brightness value predetermined in advance.

In this case, the second region of therapy (ROT2) may be considered as a portion required intensive care compared to the first region of therapy (ROT1).

In this embodiment of the present invention, it is referred to as the first point X1 for a boundary point between the second region of normal (RON2) and the first region of therapy (ROT1) on the guide path (GP) as sequentially moving at the starting point Ps of the laser, the second point X2 for a boundary point between the first region of therapy (ROT1) and the second region of therapy (ROT2), the third point X3 for a boundary point between the second region of therapy (RON2) and the second region of normal (ROT2), the fourth point X4 for a boundary point between the second region of normal (RON2) and the first region of therapy (ROT1), the fifth point X5 for a boundary point between the first region of therapy (ROT1) and the second region of therapy (ROT2), the sixth point X6 for a boundary point between the second region of therapy (ROT2) and the first region of therapy (ROT1), the seventh point X7 for a boundary point between the first region of therapy (ROT1) and the second region of therapy (ROT2), and the eighth point X8 for a boundary point between the second region of therapy (ROT2) and the first region of therapy (ROT1).

Figure 17:
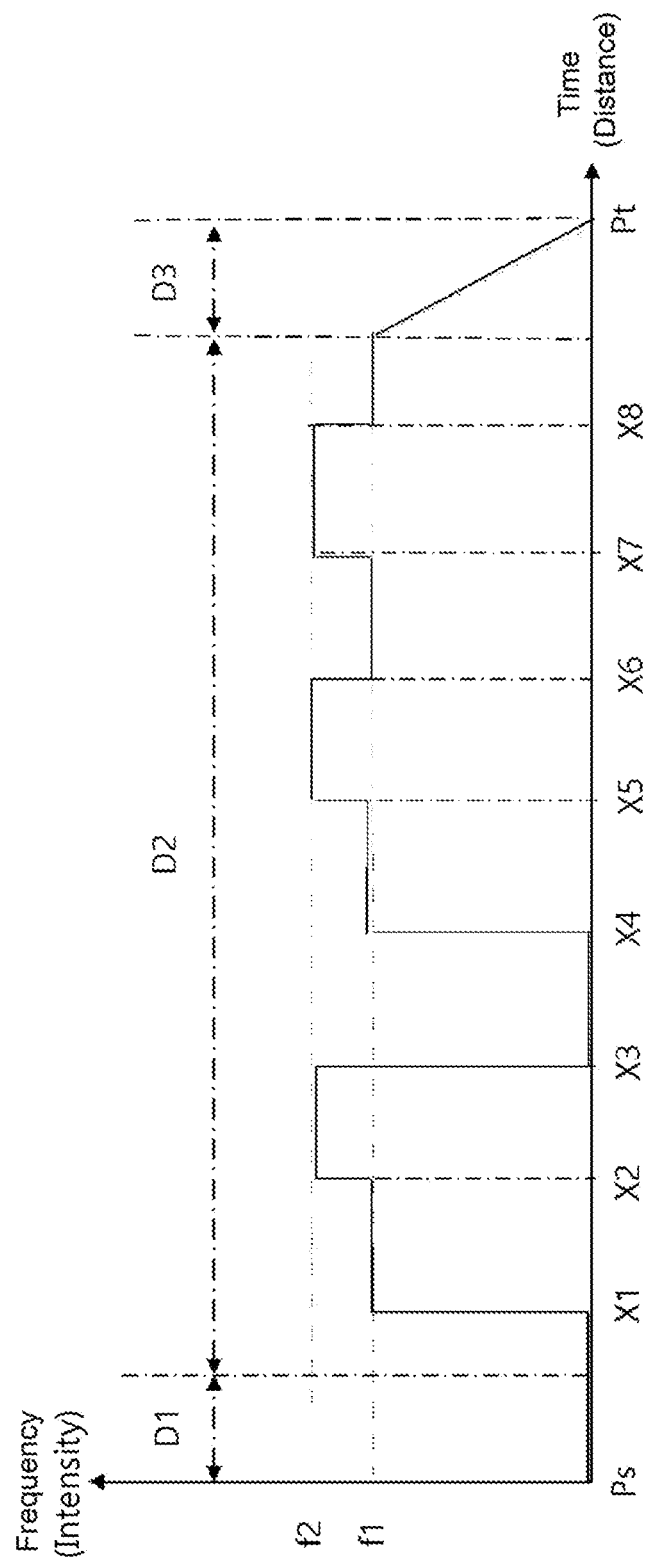
Figure 18:
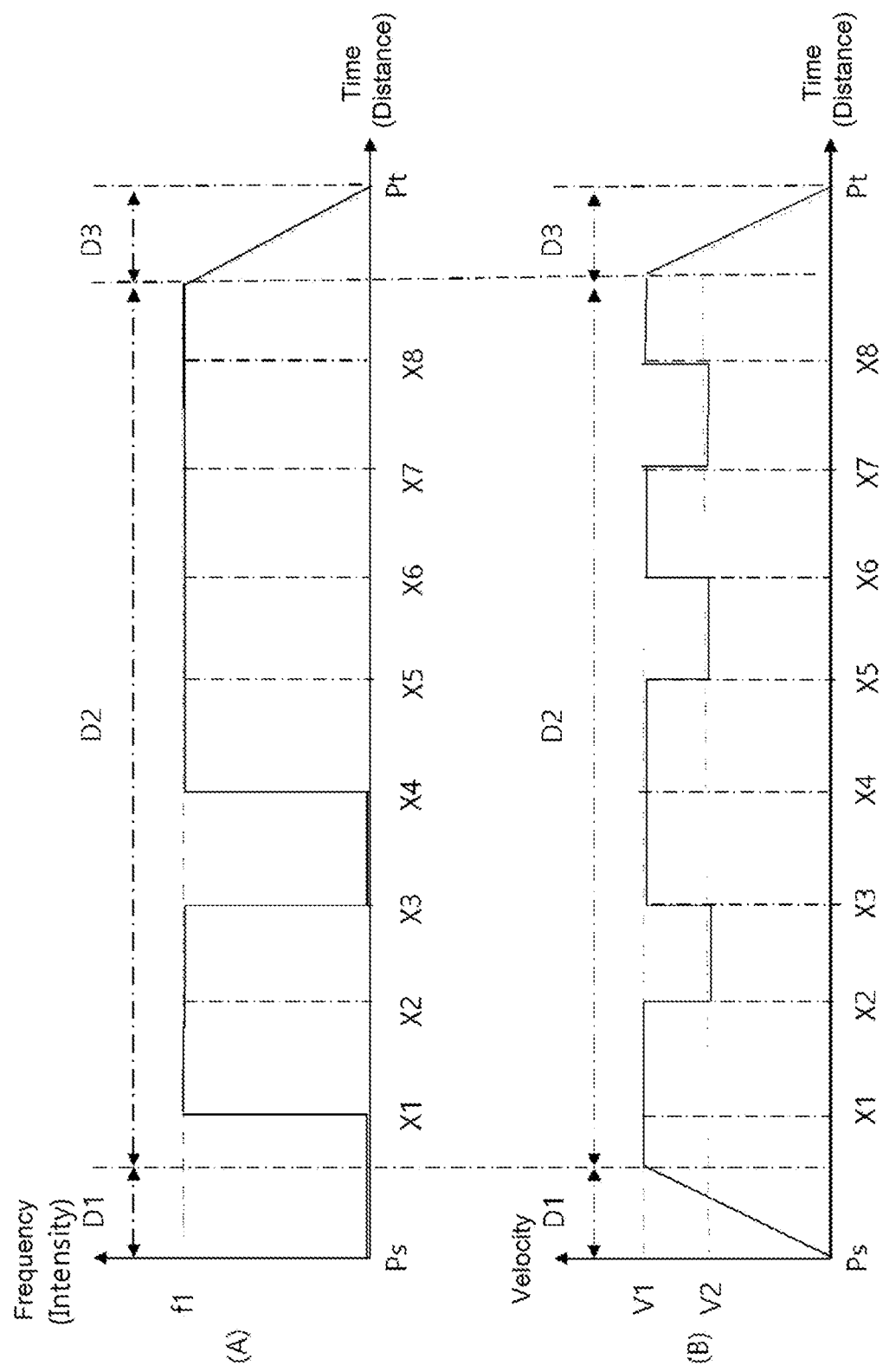
Figure 19:
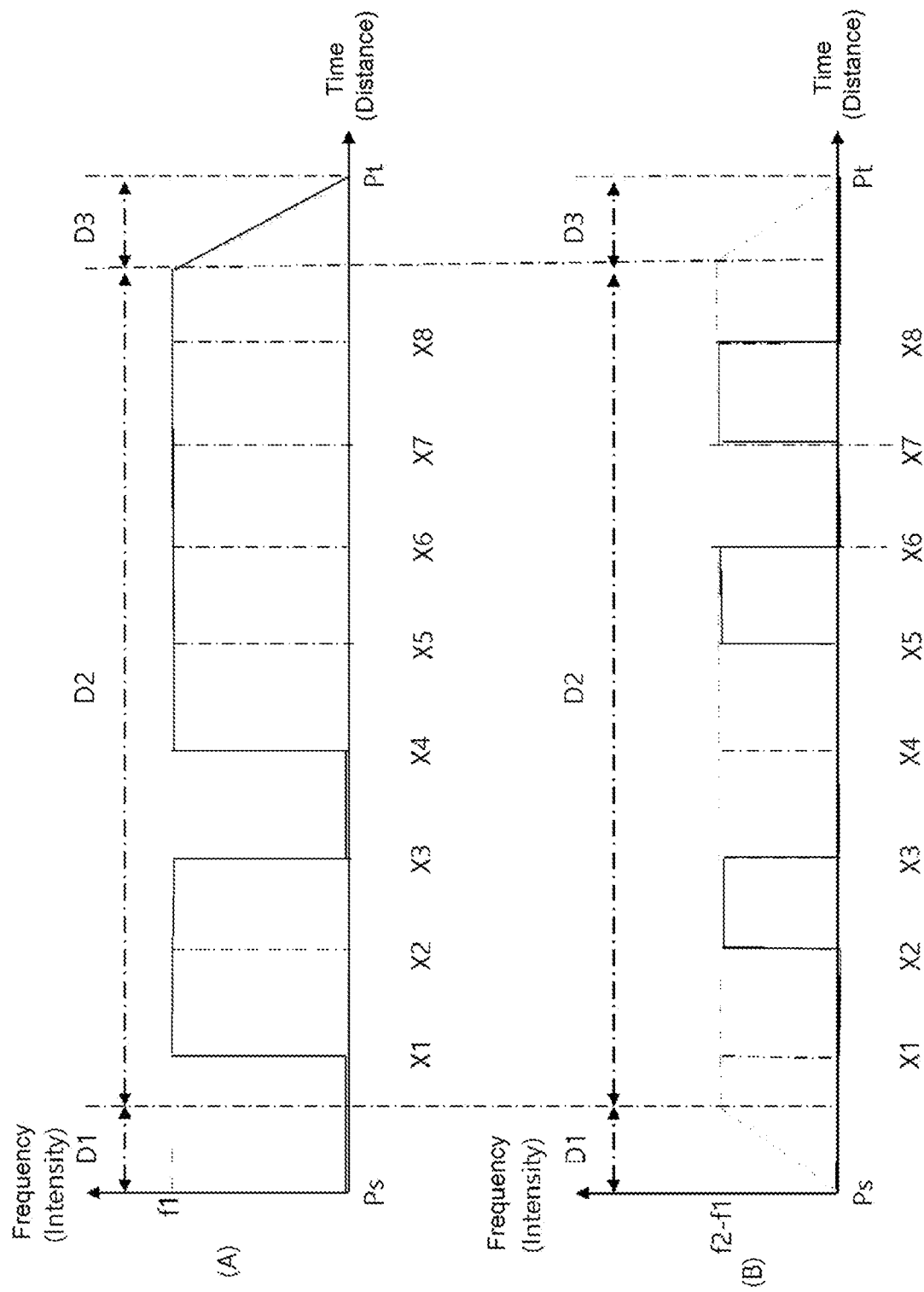

As shown in FIG. 17, the robot arm may turn off the laser irradiation in sections from the start point (Ps) of the laser to the first point (X1) and from the third point (X3) to the fourth point (X4), respectively.

For example, since Ps-X1 section and X3-X4 section are included in the second region of normal (RON2), thus the robot arm 100 may not irradiate the laser.

On the other hand, the frequency of the laser is set at the first frequency (f1) in X1-X2 section, X4-X5 section, X6-X7 section and the section from the eighth point (X8) to the beginning of the deceleration section (D3).

And, it may be gradually varied the gradation of the irradiation conditions through the variations of the laser irradiation intensity or laser irradiation frequency by the variation in velocity of the end-effector 101, or the adjustment of the maximum unit area (fluence) or pulse duration of the laser in X1, X3 and X4 points.

Further, in the other points except X1, X3 and X4 points, the gradation of the irradiation conditions as described above may be gradually achieved.

On the other hand, in X2-X3, X5-X6, and X7-X8 sections, the frequency of the laser may set with a second frequency (f2) that is higher than the first frequency (f1).

In this case, the laser, which is relatively stronger, may be irradiated on the second region of therapy (ROT2) thereby improving the treatment efficiency.

In the above, an embodiment of the present invention has been described by changing the frequency of the laser to adjust the intensity of the laser, but it may be possible to adjust the treatment intensity by changing the emission intensity of the laser in addition to the frequency.

Referring to FIG. 18(A), the frequency of the laser may equally set as the first frequency (f1) in X1-X3 section, X4-X8 section and a section from the eighth point (X8) to the beginning of the deceleration section (D3).

Thus, while maintaining the frequency of the laser, as shown in FIG. 18(B), the movement speed of the robot arm 100 may set at the first speed (V1) in a section from a point of the end of the acceleration section (D1) to the second point X2, X3-X5 section, X6-X7 section, and the section from the eighth point (X8) to the beginning of the deceleration section (D3).

On the other hand, the movement speed of the robot arm 100 may be set at the second speed (V2) which is slower than the first speed (V1) in X2-X3, X5-X6, and X7-X8 sections.

In this case, the laser may irradiate relatively longer than the second region of therapy (ROT2) thereby improving the treatment efficiency, and the overlap of laser irradiation may be increased.

On the other hand, for the second region of therapy (ROT2), the number of the treatment may be set a lot more than the first region of therapy (ROT1). For this, it will be described below referring to FIG. 19.

FIG. 19(A) shows the status that the robot arm 100 may irradiate the laser for the first laser treatment on the surface of the object 400 along the guide path (GP) within the region of interest (ROI), while FIG. 19(B) shows the status that of performing the second laser irradiation carried out after the end of the first laser treatment.

Referring to FIG. 19(A), the robot arm 100 may irradiate the laser in X1-X3 section, X4-X8 section and a section from the eighth point (X8) to before the deceleration section (D3), in which the frequency of the laser may be equally set at the first frequency (f1).

Referring to FIG. 19(B), in the second course of the laser treatment, the robotic arm 100 may irradiate the laser in X2-X3 section, X5-X6 section, and X7-X8 section corresponding to the second region of therapy (ROT2), in which it may be equally set to the frequency of the laser corresponding to the difference between the second frequency (f2) and the first frequency (f1).

Thus, the therapeutic effect similar to that of irradiating the laser of the second frequency (f2) may be occurred in the second region of therapy (ROT2).

Figure 24:
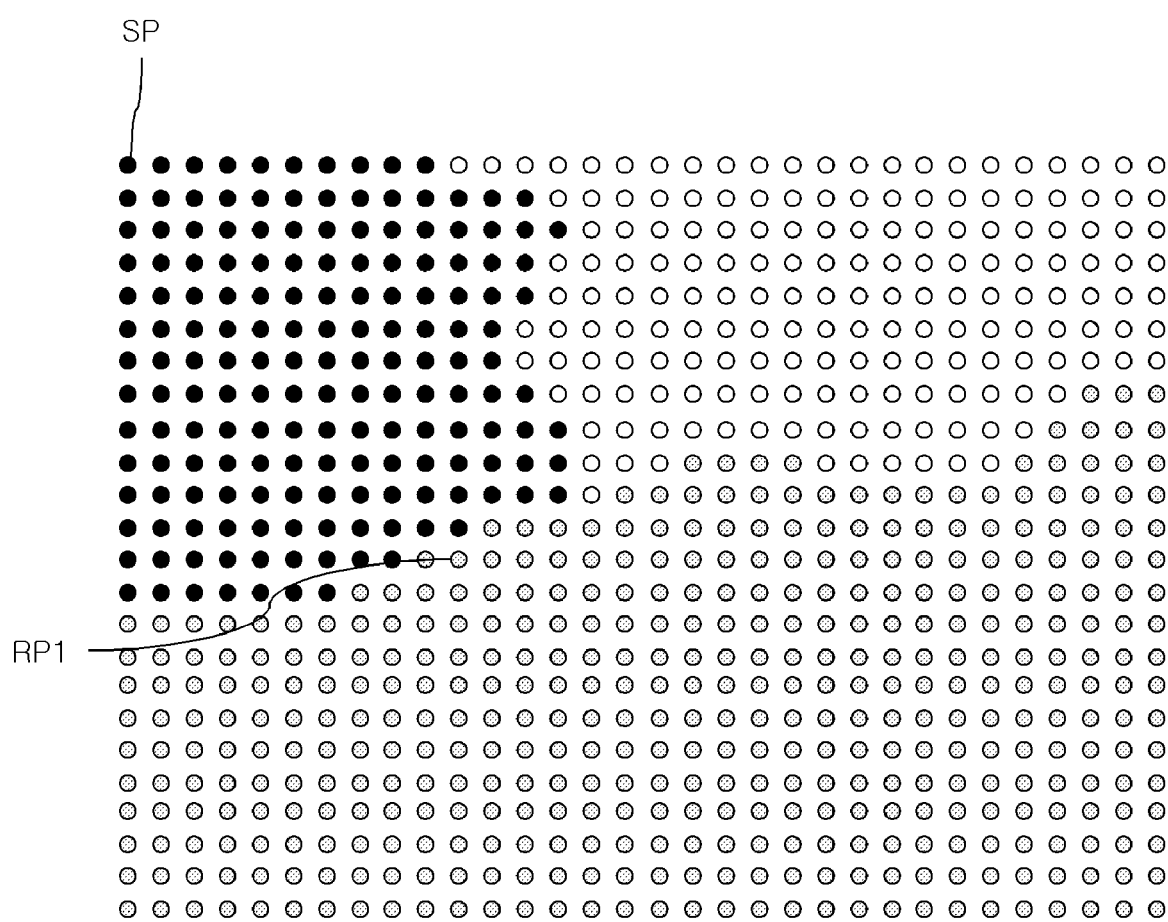

According to the present invention, as in the case of FIG. 24, the end-effector 101 of the robot arm 100 preferably irradiates the laser exactly perpendicular to the surface of the object 400 to increase the therapeutic efficacy and to improve the treatment accuracy.

To this end, the robot arm 100 may be desirable with degree of freedom (DOF). Specifically, the robot arm 100 may be more desirable to have 5 degrees of freedom, and it is preferably have at least 6 degrees of freedom for exceptional circumstances.

Figure 20:
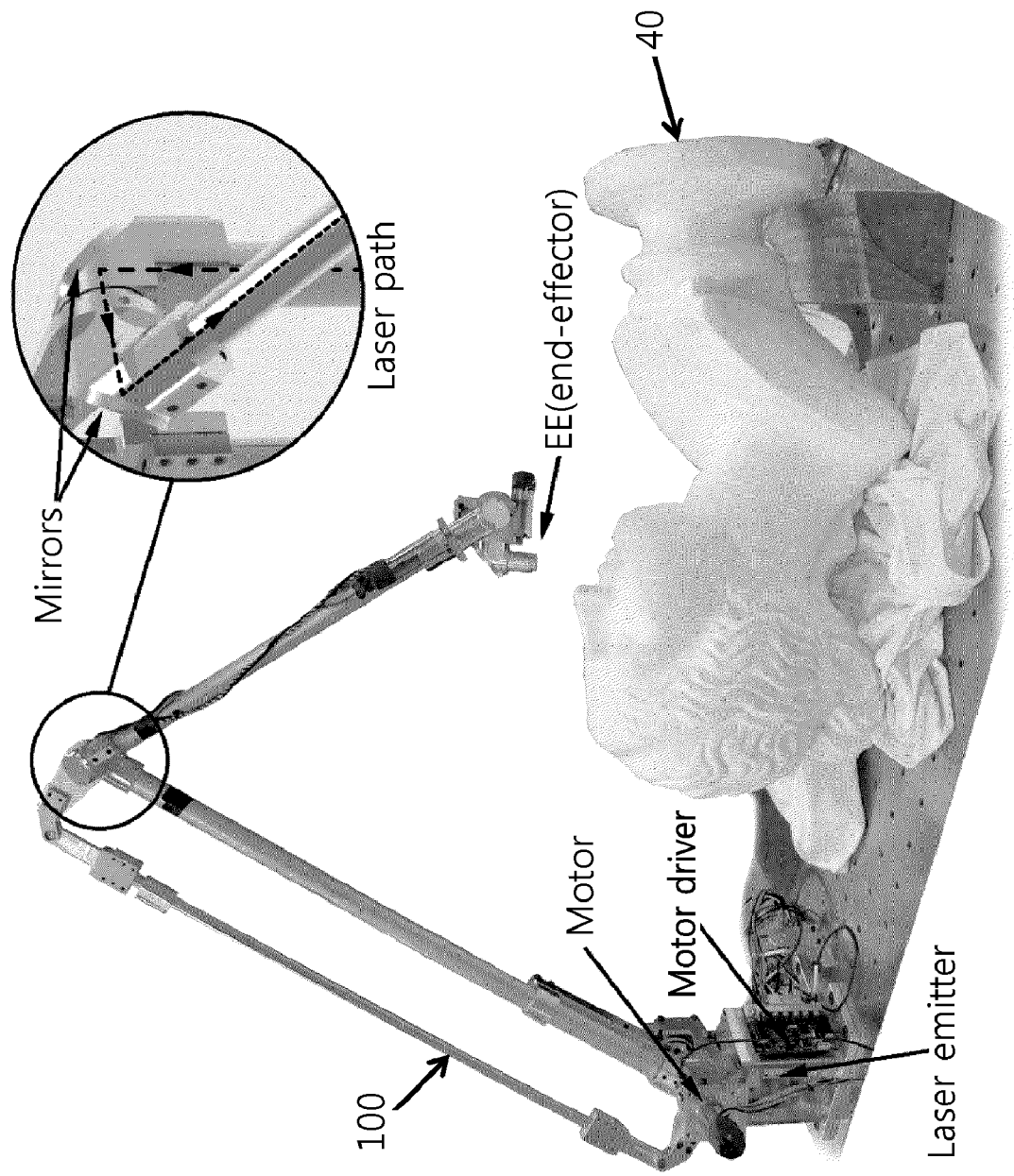
FIG. 20 is a perspective view showing the constitution of a laser treatment apparatus according to embodiments of the present invention.

FIG. 20 illustrates the structure of the laser treatment apparatus according to an embodiment of the present invention. The laser treatment apparatus includes a laser emitter, a motor, a motor drive, a reflection mirror, and an end effector (EE) irradiate the laser onto the surface of the object 400, that is the plaster cast of the head shape.

The laser treatment apparatus shown in FIG. 20 according to an embodiment of the present invention may have one or more components omitted or added.

For example, when the laser is delivered to the end effector (EE) using an optical fiber, the reflective mirror may be omitted.

Referring to FIG. 20, the motor and the motor drive operate the robot arm 100. When the laser emitter irradiates the laser, the reflection mirror reflects the laser at a predetermined angle to reach the end-effector (EE), the end-effector (EE) connected to the end terminal of the robot arm 100 may irradiate the laser on the surface of the object 400.

For example, the motor and the motor drive may be controlled by the motion controlling unit 220 so that the end-effector (EE) is moved along the guide path (GP) set by the vision controlling unit 210.

In addition, the laser emitter may be controlled by the motion controlling unit 220 so that the laser is irradiated onto the laser irradiation points set by the vision controlling unit 210.

As shown in FIG. 20, when the robot arm 100 having a predetermined degree of freedom is operated to sequentially irradiate the laser along the guide path (GP) on the surface of the object through the end-effector (EE), it is preferable to set the guide path (GP) so that the operation of the robot arm 100 may be easily controlled.

For example, it is preferable that the motion of the robot arm 100 or the motion pattern of the end-effector (EE) may be continuous, and the speed variation is minimized. In this case, it may be precisely controlled according to the guide path (GP) previously set and the laser irradiation points.

Meanwhile, as described above, in order to enhance the effect and accuracy of treatment, the end effector 101 of the robot arm 100 can irradiate a laser exactly perpendicular to a surface of the object 400. To this end, a normal vector can be obtained for each of points on the object (such as face) to be treated by laser irradiation.

However, when the laser is to be irradiated exactly perpendicular to the surface of the object according to the normal vector for each of points on the object, the movement of the end effector 101 of the robot arm 100 or joints constituting the robot arm 100 becomes very large and fast. Thus, the resulting vibration may lower the accuracy and increase the anxiety of a user such as patient or doctor.

According to an embodiment of the present invention, by grouping points on the surface of the object according to a similarity between angles of the normal vectors to generate a closed curve and divide the area of the object into a plurality of treatment regions for laser irradiation, such vibration due to the excessive movement of a laser treatment apparatus can be reduced.

In particular, as described referring to FIG. 20, when irradiating a laser using a robot arm with an end effector which serves to irradiate the laser, the movement of the end effector and the resulting vibration are reduced. Thus, the accuracy of laser irradiation can be further improved, and a patient can be treated in a more comfortable state.

Figure 21:
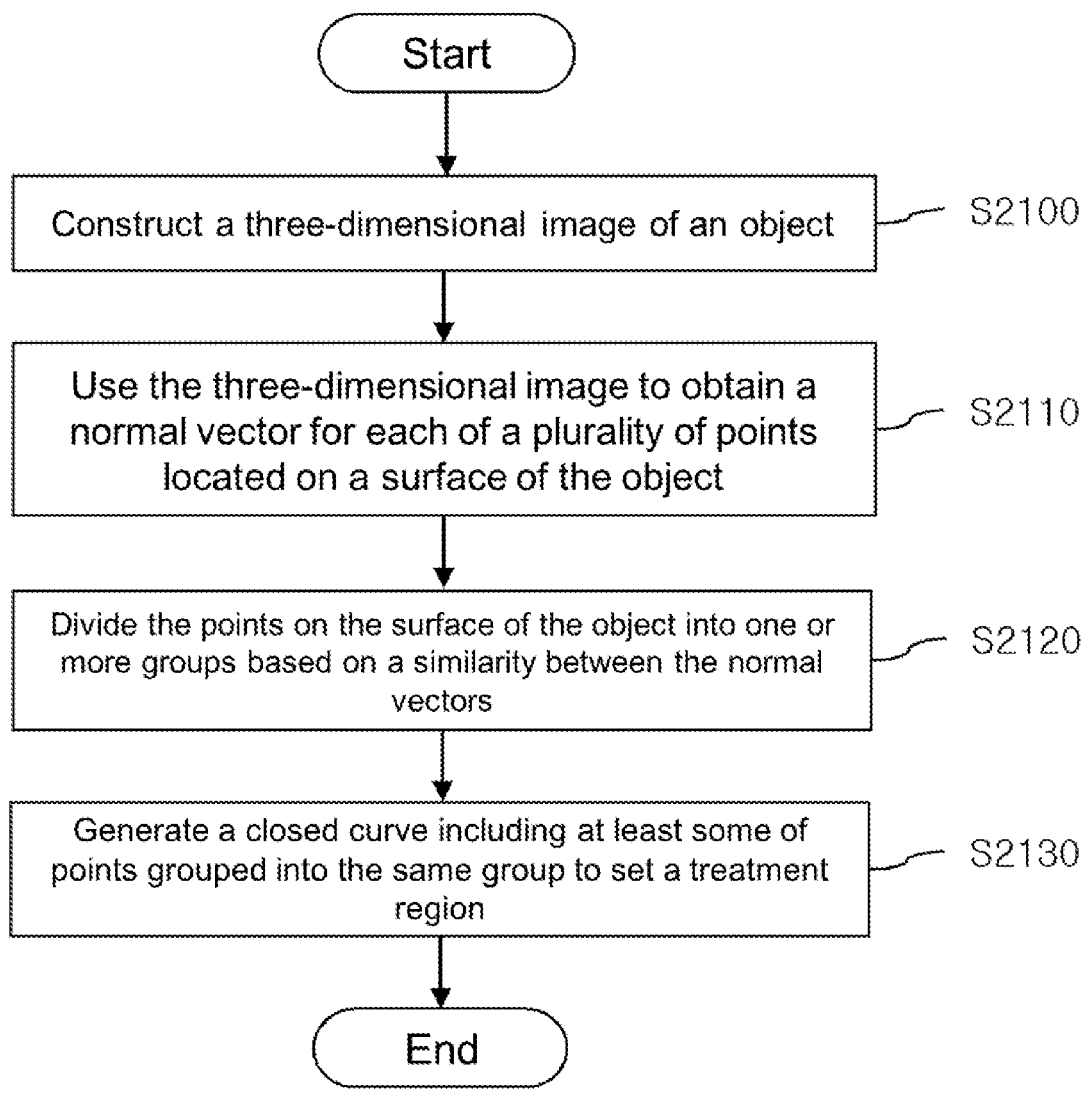
FIG. 21 is a flowchart showing a region division method for laser treatment according to an embodiment of the present invention.

FIG. 21 is a flowchart illustrating a region division method for laser treatment according to an embodiment of the present invention. Now, the region division method will be described in conjunction with the block diagram illustrating the configuration of the laser treatment apparatus according to an embodiment of the present invention as shown in FIG. 1. Meanwhile, in describing the region division method for laser treatment, the matters as described with reference to FIGS. 1 to 20 will not be described again below.

Now, referring to FIG. 21, the vision controlling unit 210 constitutes a three-dimensional image of an object (Step S2100), and uses the three-dimensional image to obtain a normal vector for each of a plurality of points located on a surface of the object (Step S2110).

For example, data acquired and output from the scanner 300 such as 3D camera may include location and color information (such as RGB data) for each of the plurality of points located on the surface of the object.

In this case, the vision controlling unit 210 may use the location information and the RGB color information to calculate a normal vector for each of the plurality of points. Without a limitation, the normal vector can be calculated using RANSAC (RANdom SAmple Consensus) algorithm.

Then, the vision controlling unit 210 divides points on the surface of the object into one or more groups based on a similarity between the obtained normal vectors (Step S2120).

For example, the vision controlling unit 210 groups points whose angles of the normal vectors are within a threshold range into one group, so that points on the surface of the object may be grouped into a plurality of groups having similar angles of the normal vectors.

Here, the threshold may be changed based on at least one of a treatment aim, a treatment site, a treatment time, an object's condition, and a user's setting, and may be set to change the minimum number of points grouped into one group.

That is, as the threshold increases, the number of groups dividing points on the surface of the object may be smaller. On the contrary, as the threshold decreases, the number of groups may be larger.

In addition, as the minimum number of points grouped into one group is increased, the number of groups dividing points on the surface of the object may be smaller. On the contrary, as the minimum number of points grouped in the one group is decreased, the number of groups may be larger.

Since the threshold are related to the accuracy of treatment and the required time, the value may be selected or adjusted by a user in consideration of the relations described above, or alternatively may be automatically set.

More particularly, in consideration that an amount of energy transferred per unit area is changed according to an angle at which a laser is incident on a surface of an object to be treated, a threshold used to divide points on the surface of the object may be set.

For example, when the profile of a laser beam is a top hat model, if the laser is irradiated exactly perpendicular to skin surface, the cross-section of a laser irradiation region on the skin surface forms a circle, but if the laser is irradiated on the skin surface at any incident angle θ, the cross-section of a laser irradiation region forms an ellipse that a cylinder is diagonally cut.

In this case, the cross-sectional area A of the laser irradiation region on the skin surface may be calculated by Equation 1 according to an incident angle θ to which the laser is irradiated to skin.

$$A = \pi r^2 \sec\theta = \pi r^2 \frac{1}{\cos\theta} \quad \text{[Equation 1]}$$

In accordance to Equation 1, an amount of energy transferred per unit area in the skin surface is changed depending on the incident angle θ to which the laser is irradiated to skin, and more particularly the amount is proportional to a cosine value (cosθ) of the incident angle θ.

Thus, assuming that the source of laser is stable and homogeneous, and energy per unit time and a beam size generated from the laser beam are constant, energy per unit area transferred to skin may be determined by the incident angle θ to which the laser is irradiated to skin.

The following Table 1 shows the cross-sectional area of the laser irradiation region on the skin surface and the ratio of energy transferred per unit area with respect to the incident angle θ to which the laser is irradiated to skin.

TABLE 1

| Incident angle | 0° | 5° | 10° | 20° | 30° |
|---|---|---|---|---|---|
| Energy | 1 | 1 | 1 | 1 | 1 |
| Irradiated cross-sectional area | 1 | 1.0038 | 1.0154 | 1.0642 | 1.1547 |
| Energy per unit area | 1 | 0.9962 | 0.9848 | 0.9397 | 0.8660 |

As can be seen in Table 1, as an angle at which a laser is incident on a surface of an object (such as skin) increases, the cross-sectional area of a region to which the laser is irradiated increases, thereby reducing energy transferred per unit area in the surface of the object.

That is, when the incident angle of laser is 5°, the energy transferred per unit area in the surface of the object is reduced by about 0.4% compared to the case where the incident angle is 0°.

When the incident angle of laser is 10°, the energy transferred per unit area in the surface of the object is reduced by about 1.5% compared to the case where the incident angle is 0°.

Further, when the incident angle of laser is 20°, the energy transferred per unit area in the surface of the object is reduced by about 6% compared to the case where the incident angle is 0°.

When the incident angle of laser is 30°, the energy transferred per unit area in the surface of the object is reduced by about 13.4% compared to the case where the incident angle is 0°.

As described above, in consideration that energy transferred per unit area is not linearly and inverse-proportionally reduced with increasing the incident angle of laser, a threshold used to divide points on the surface of the object may be properly set according to a treatment effect, a treatment aim or a treatment time.

For example, when one wishes to accurately set an error of laser treatment effect within 1%, a threshold used to divide points on a surface of an object can be set to 5°.

Meanwhile, when one wishes to set an error of laser treatment effect within 10% and reduce a treatment time, a threshold used to divide points on a surface of an object can be set to 20°.

Also, the vision controlling unit 210 generates a closed curve including at least some of points grouped into the same group to set a region to be treated (Step S2130).

For example, for each of groups in which points on a surface of an object are grouped, the vision controlling unit 210 may generate a single closed curve within which points belonging to that group exist, so that a plurality of treatment regions may be generated, which corresponds to each of a plurality of groups.

However, in consideration of the shape or complexity of single closed curve, the vision controlling unit 210 may generate a single closed curve within which some of points belonging to a particular group exist, thereby setting a region to be treated.

Figure 22:
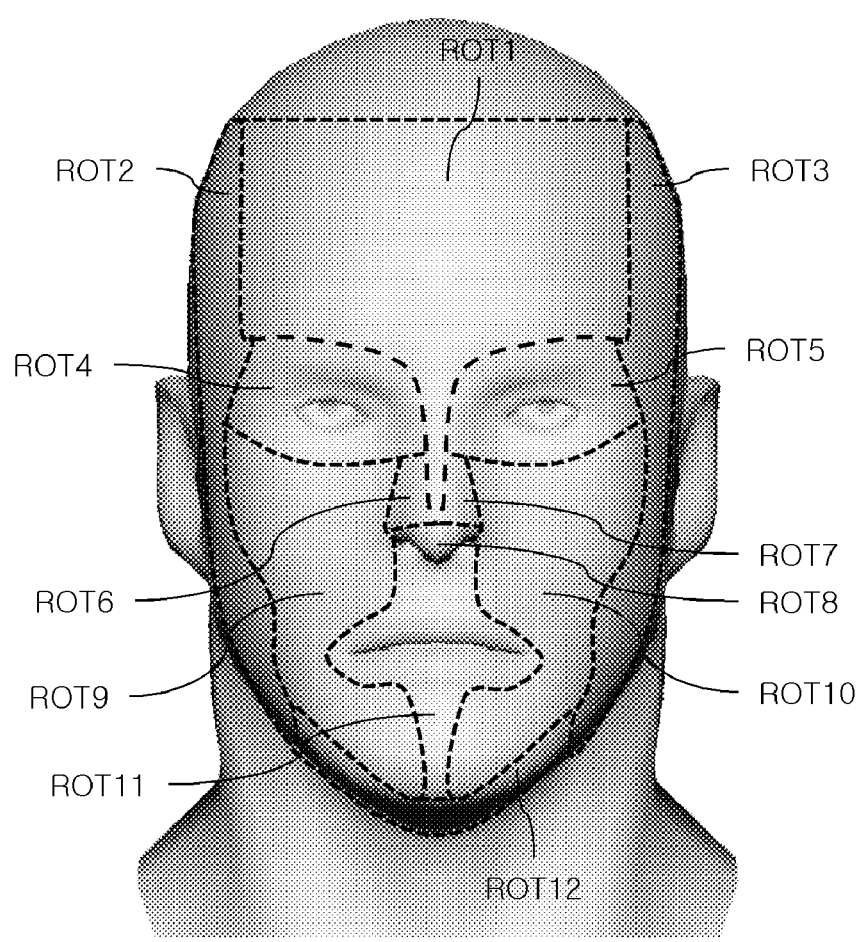
FIG. 22 is a view showing an embodiment of the divided plurality of treatment regions.

FIG. 22 shows an embodiment for a plurality of treatment regions which are divided according to the region division method as described above, as a result of dividing an area of face, an object to be treated, into a plurality of treatment regions ROT1 to ROT12 based on a similarity between normal vectors of points on a surface.

As shown in FIG. 22, after the area of face is divided into the treatment regions ROT1 to ROT12 having similar angles of the normal vectors, any one of the plurality of treatment regions ROT1 to ROT12 may be selected by a user, and subsequently a laser may be irradiated on the selected region.

During the laser is irradiated on the selected treatment region, since angles of normal vectors for inner points are similar within a threshold range, an end effector or a robot arm may not be moved to irradiate the laser on the face surface in a vertical direction, but the end effector can continuously irradiate the laser at a constant angle.

Meanwhile, when irradiating a laser to different treatment regions among the treatment regions ROT1 to ROT12, an angle at which the laser is irradiated from an end effector may be changed according to a reference value of a normal vector of that treatment region.

For example, while treatment for the first treatment region ROT1 is performed, an angle at which a laser is irradiated from an end effector is set to a first value adjusted to a mean value, a median value or a separate optimum value of normal vector angles of points in the treatment region ROT1, and the first value can be constantly maintained without being changed.

Then, while treatment for the second treatment region ROT2 is performed, an angle at which a laser is irradiated from an end effector is set to a second value adjusted to a mean value, a median value or a separate optimum value of normal vector angles of points in the treatment region ROT2, and the second value can be constantly maintained without being changed.

In addition, the order of treatment for all or some of the plurality of treatment regions ROT1 to ROT12 may be set by a user or by an automatic manner, where the order of treatment may be determined to have a trend that adjacent regions among the treatment regions ROT1 to ROT12 are non-continuous.

FIGS. 23 to 33 explain embodiments for a method of dividing a treatment region based on a similarity between normal vectors of points on a surface of an object. For the simplicity of the description, an object having a rectangular area is described as an example, but the present invention is not limited thereto.

Figure 23:
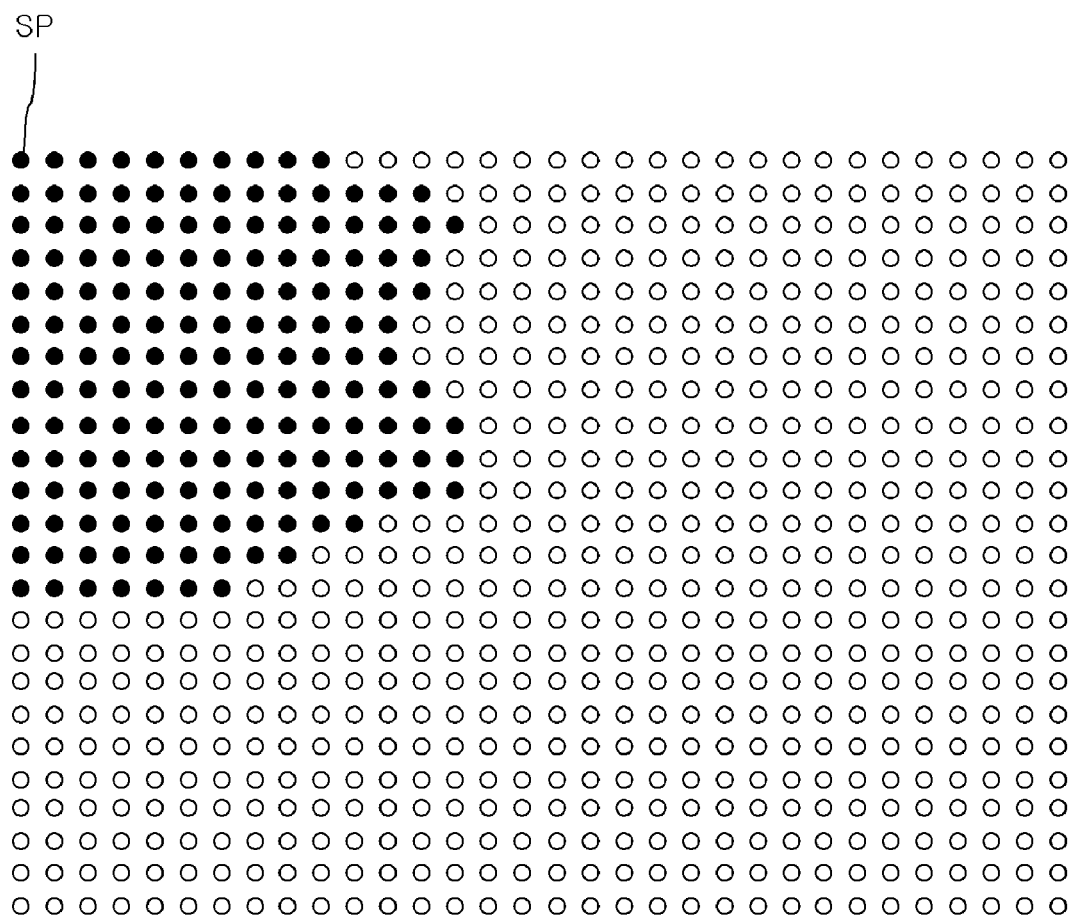
FIGS. 23 to 27 are views for explaining embodiments of a method of dividing treatment regions based on a similarity between normal vectors for points on the surface of the object.

Referring to FIG. 23, any one of points on a surface of the object is set as a starting point SP, and subsequently an angle between normal vectors for the starting point SP and peripheral points located around the starting point SP can be obtained.

As a result, when the obtained angle is equal to or less than a predetermined threshold, the peripheral points may be grouped into a first group which is the same as the starting point SP.

That is, by selecting peripheral points in which an angle between normal vectors with the starting point SP is equal to or less than a predetermined threshold, as described above, among points around the starting point SP, points including the starting point SP may be grouped as the first group as shown in FIG. 23.

Here, the starting point SP may be randomly set from points on the surface of the object, or may be selected by a user.

In addition, the starting point SP may be set to a point in a particular site of face which is recognized using a face recognition algorithm, and in this case, a point which corresponds to a particular site such as nose, forehead or mouth on a two-dimensional image of face recognized using a three-dimensional image may be designated as the starting point SP.

Then, any one of the remaining points which are not grouped into the first group is set as a reference point RP, and points having similar angles of normal vectors relative to the reference point may be grouped into another group.

Now, referring to FIG. 24, any one point adjacent to the outermost point in points which are grouped into the first group is set as a first reference point RP1, and subsequently an angle between normal vectors for the first reference point RP1 and peripheral points located around the first reference point (points not included in the first group) can be obtained.

As a result, when the obtained angle is equal to or less than a predetermined threshold, the peripheral points may be grouped into a second group which is the same as the first reference point RP1.

That is, by selecting peripheral points in which an angle between normal vectors with the first reference point RP1 is equal to or less than a predetermined threshold, as described above, among points around the first reference point RP1, points including the first reference point RP1 may be grouped as the second group as shown in FIG. 24.

Figure 25:
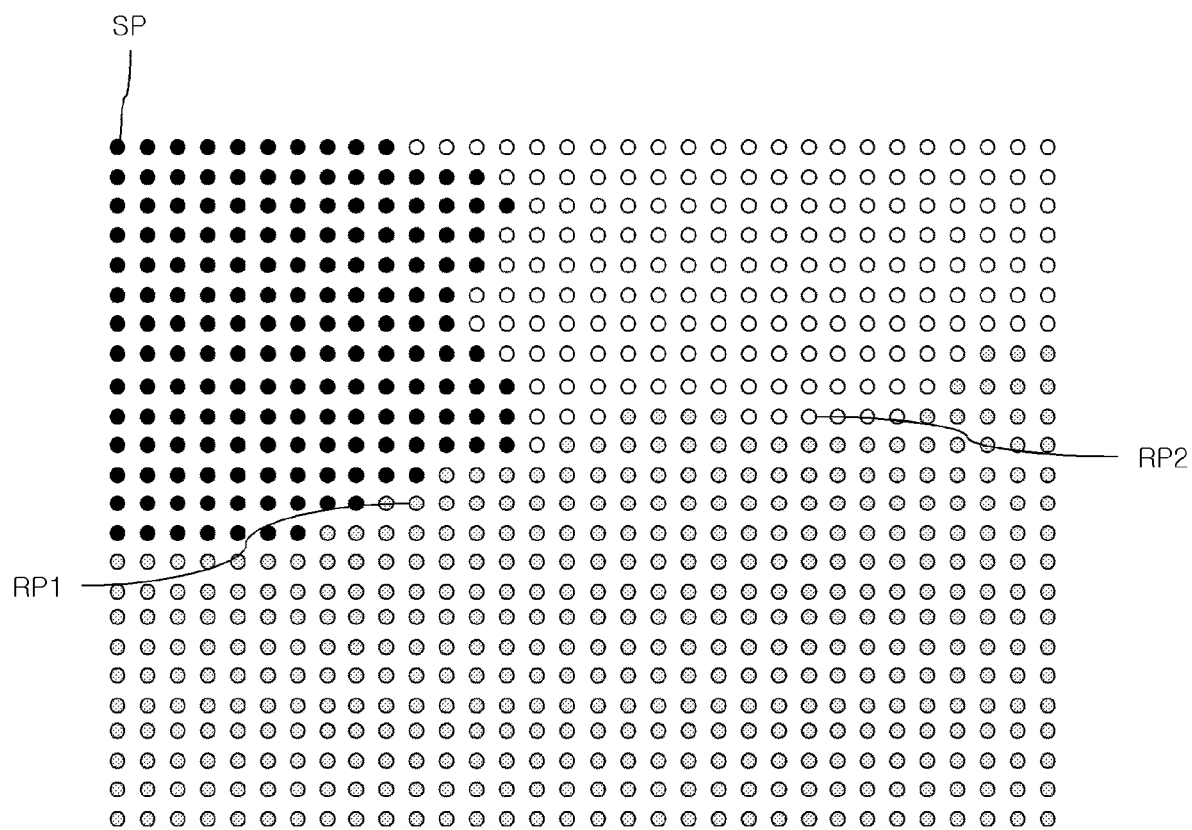

Referring to FIG. 25, any one point adjacent to the outermost point in points which are grouped into the second group is set as a second reference point RP2, and subsequently an angle between normal vectors for the second reference point RP2 and peripheral points located around the second reference point (points not included in the first and second groups) can be obtained.

As a result, when the obtained angle is equal to or less than a predetermined threshold, the peripheral points may be grouped into a third group which is the same as the second reference point RP2.

That is, by selecting peripheral points in which an angle between normal vectors with the second reference point RP2 is equal to or less than a predetermined threshold, as described above, among points around the second reference point RP2, points including the second reference point RP2 may be grouped as the third group as shown in FIG. 25.

As described above, after points on the surface of the object are divided into the first, second and third groups, treatment regions corresponding to each of the first, second and third groups may be set.

Figure 26:
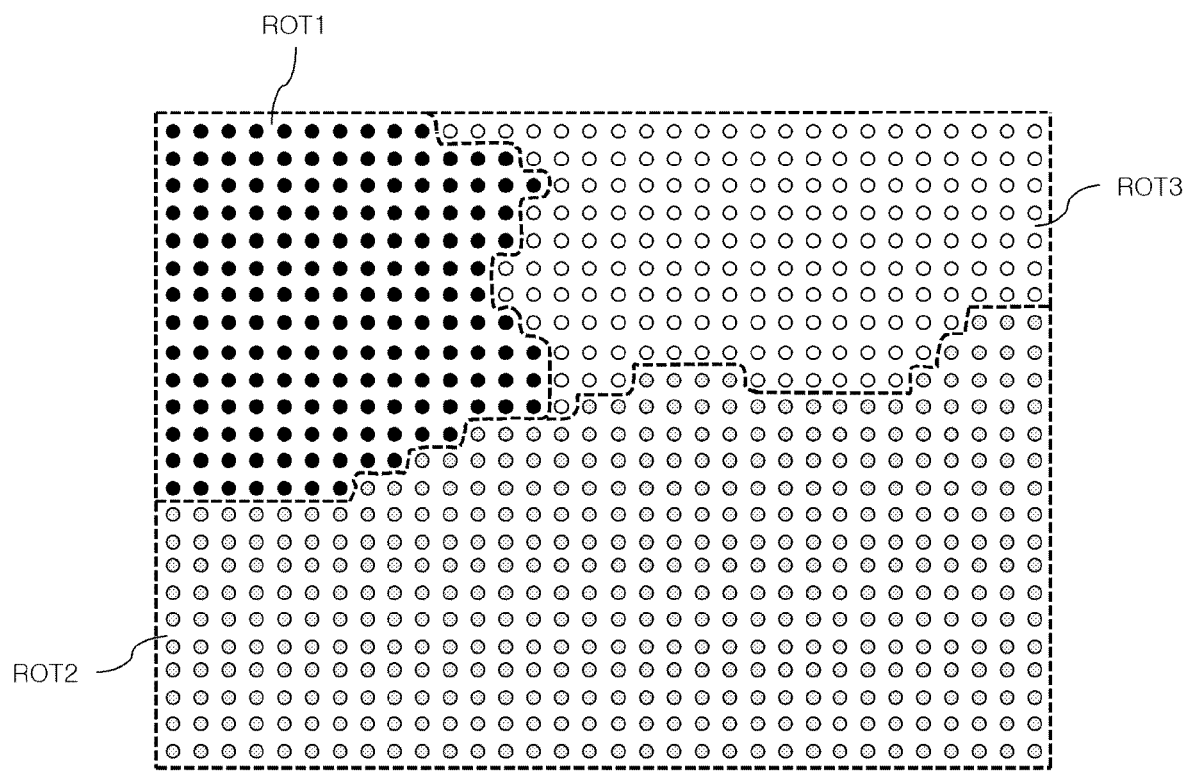

Referring to FIG. 26, the first treatment region ROT1 may be set by generating a single closed curve including points of the first group; the second treatment region ROT2 may be set by generating a single closed curve including points of the second group; and the third treatment region ROT3 may be set by generating a single closed curve including points of the third group.

To set a treatment region, if necessary, a single closed curve including some of points of a particular group or even points of other groups may be generated.

Figure 27:
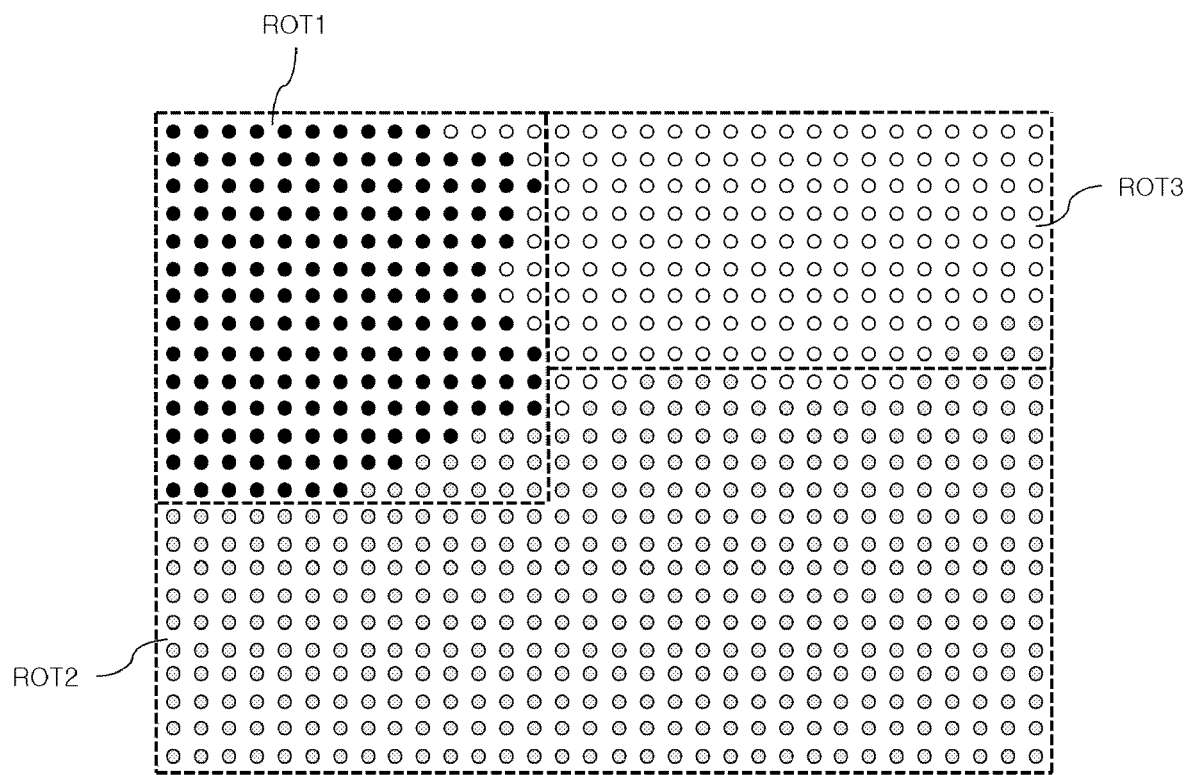

Referring to FIG. 27, a rectangular-shaped single closed curve may be generated to set the treatment regions ROT1 to ROT3, and in this case, the movement of an apparatus may be further simplified.

Meanwhile, point clouds on a surface of face may be displayed on a screen according to data output from a 3D camera, and a normal vector (more particularly, an angle of the normal vectors) for each of the points may be represented by different colors.

That is, the result of grouping points on the face surface based on a similarity between normal vector angles may be represented by colors, and points represented with the same color are included in the same group, which have similar angles of normal vectors within a threshold range.

For example, a threshold for grouping points into the same group may be set to 20° and the minimum number to be grouped into one group may be set to 5 points.

In addition, a threshold for grouping points into the same group may be set to 5° and the minimum number to be grouped into one group may be set to 1 point.

Here, if the threshold and the minimum number of points to be grouped into one group are decreased, the number of groups may be increased.

Meanwhile, a threshold for grouping points into the same group may be set to 10° and the minimum number to be grouped into one group may be set to 5 points.

Further, a threshold for grouping points into the same group may be set to 30° and the minimum number to be grouped into one group may not be limited.

A user may select a desired treatment region using a pointer from treatment regions formed by points divided into a plurality of groups Further, a user may determine the order of treatment for at least some of treatment regions formed by points divided into a plurality of groups.

In this case, according to the order thus determined, laser irradiation may be sequentially performed for each treatment region. That is, a laser is irradiated on irradiation points within a treatment region designated as No. '1' at a first angle from an end effector to complete treatment for that treatment region. Then, the laser is irradiated on irradiation points within a treatment region designated as No. '2' at a second angle from the end effector to complete treatment for that treatment region. Then, the laser is irradiated on irradiation points within a treatment region designated as No. '3' at a third angle from the end effector to complete treatment for that treatment region. Finally, the laser is irradiated on irradiation points within a treatment region designated as No. '4' at a fourth angle from the end effector to complete treatment for that treatment region, thereby completing the entire treatment.

Meanwhile, the order of treatment may be determined to have a trend that adjacent regions among the plurality of treatment regions are non-continuous.

This is to prevent skin deterioration due to energy overlap when a laser is continuously irradiated to adjacent treatment regions.

Even if a user does not directly determine the order of treatment for treatment regions, the order of treatment may be automatically determined according to the criteria as described above.

According to another embodiment of the present invention, the guide path (GP) passes through both the inside and outside of the region of therapy (ROT), and the robot arm 100 is operated at a constant moving speed and by the laser scanning frequency. Therefore, the motion of the robot arm 100 or the motion pattern of the end-effector (EE) may be performed with continuous and the speed control may be facilitated.

Hereinafter, embodiments for a method of irradiating a laser while moving each treatment region will be described with reference to FIGS. 28 to 34.

Figure 28:
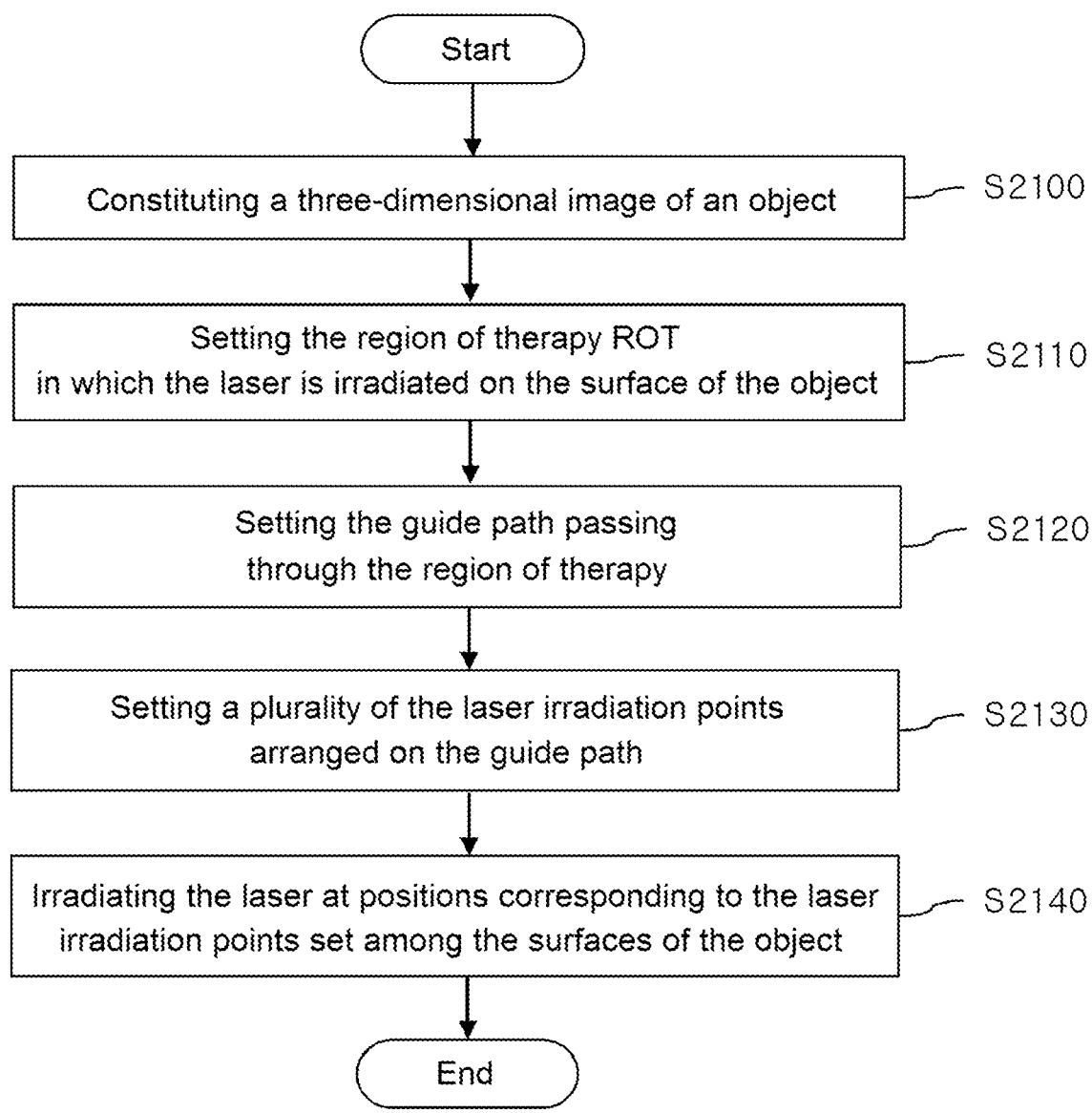
FIG. 28 is a flowchart showing a laser treatment method according to an embodiment of the present invention.
Figure 30:
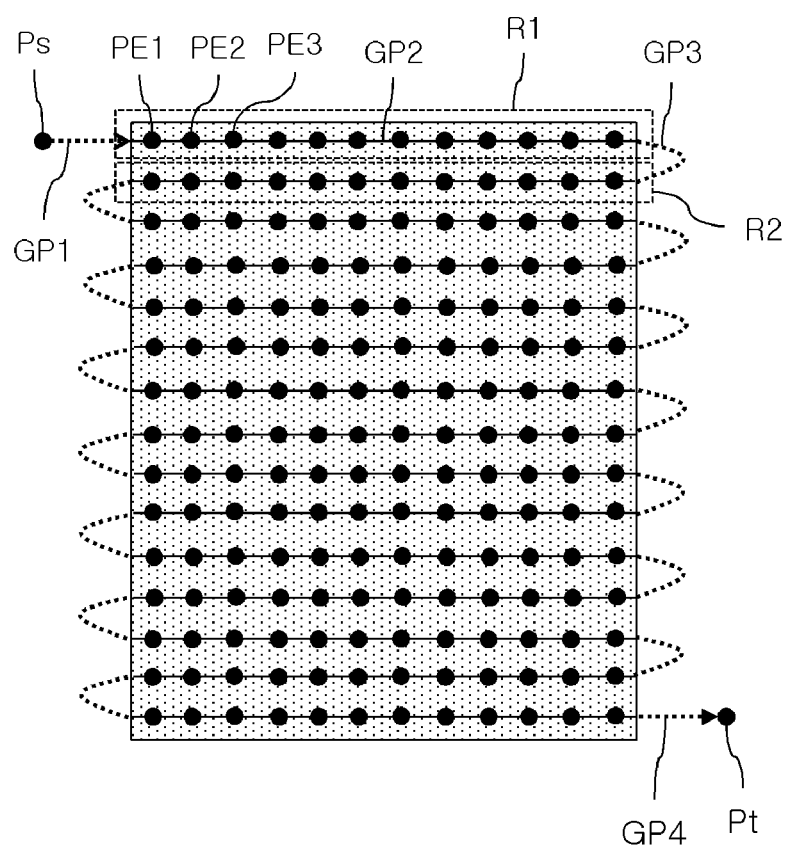

FIG. 28 is a flowchart illustrating the method of controlling the motion pattern for the laser treatment according to an exemplary embodiment of the present invention. Referring to FIG. 30, the method of controlling the motion pattern of the laser treatment apparatus will be described in connection with a block diagram of the configuration of the embodiment of the present invention. In the meantime, the description of the motion pattern control method for the laser treatment, which is the same as that described with reference to FIGS. 1 to 27, will be omitted hereunder.

Referring to FIG. 28, the vision controlling unit 210 constitutes the three-dimensional image of an object (step S3600), and sets the region of therapy (ROT) in which the laser is irradiated on the surface of the object using the three-dimensional image (Step S3610).

Thereafter, the vision controlling unit 210 sets the guide path passing through the region of therapy (ROT) (step S3620), and sets the plurality of the laser irradiation points arranged on the guide path (GP) (step S3630).

The guide path (GP) set in step S3620 may include the first section for entering the region of therapy (ROT), the second section for linearly moving at the same speed within the region of therapy (ROT), and the third section for re-entering the region of therapy (ROT) by curving and moving while changing the speed at the outside of the region of therapy (ROT).

The motion controlling unit 220 controls the robot arm 100 to irradiate the laser at positions corresponding to the laser irradiation points set at the step S3630 among the surfaces of the object (S3640).

The laser may be irradiated at a constant frequency in the second section of the guide path (GP), and the interval between adjacent laser irradiation points may be constantly maintained as the moving speed of the end effector (EE) of the robot arm 100 is constantly controlled.

FIGS. 29 to 32 are views for explaining embodiments of the guide path (GP) in which the laser unit of the robot arm 100 is moved. Hereinafter, the case where the region of therapy (ROT) has a rectangular shape is described as an example, but the shape or size of the region of therapy (ROT) may be various.

Figure 29:
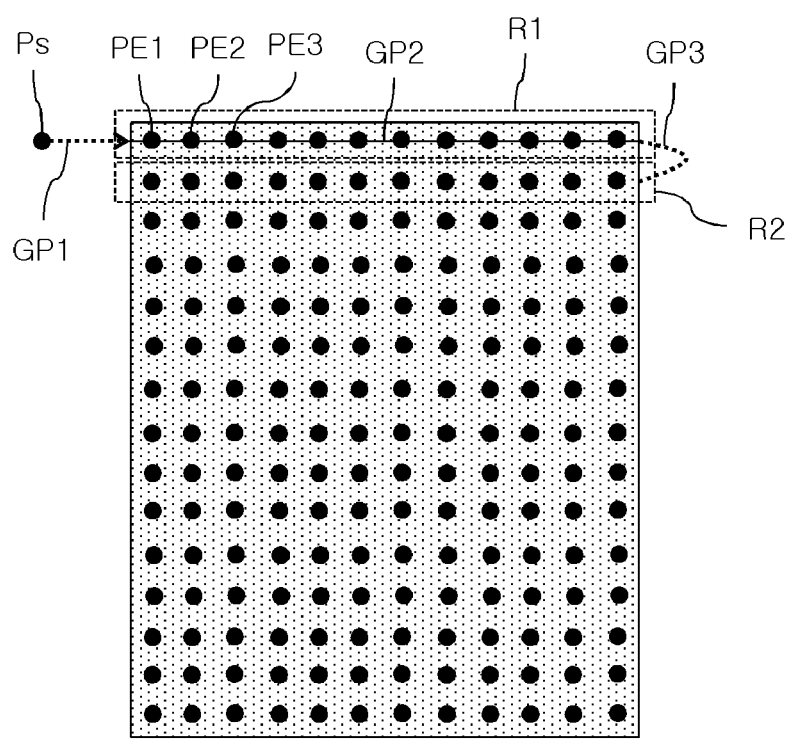
FIGS. 29 to 34 are views for explaining embodiment of a guide path in which the laser unit is moved.

Referring to FIG. 29, the laser irradiation points may be set to form the plurality of rows by horizontally and vertically arranging at regular intervals in the region of therapy (ROT).

For example, the plurality of rows of the laser irradiation points may be present in the region of therapy (ROT), since the laser irradiation points PE1, PE2, and PE3 arranged at regular intervals in the vertical direction constitute the first row R1, and the other laser irradiation points arranged in the vertical direction at regular intervals adjacent in the downward direction constitute the second row R1.

In this case, the guide path (GP) includes the first section (GP1) which moves from the starting point Ps to a constant velocity (v_1) and enters the region of therapy (ROT), the second section (GP2) that linearly moves to the region of therapy (ROT) to a constant velocity (v_2) within the region of therapy (ROT), and the third section (GP3) that curves out of the region of therapy (ROT) and re-enters the region of therapy (ROT).

In the second section (GP2) of the guide path (GP), the laser is irradiated while maintaining a predetermined frequency, and then the laser may be sequentially irradiated with the interval between the laser irradiation points previously set.

In the third section (GP3) of the guide path (GP), the laser is moved along a curved path while changing the speed from the first row (R1) of the laser irradiation points and may enter the second row (R2) immediately adjacent in the vertical direction.

For example, the moving speeds (V_1 and V_2) in the first section (GP1) and the second section (GP2) of the guide path (GP) may be equal to each other, and the moving speed in the third section (GP3) of the guide path (GP) is gradually decreased from the moving speed (V_2) in the second section (GP2) to the constant speed (V_3) to be moved to the farthest position from the region of therapy (ROT), and is gradually increased from the constant speed (V_3) in the third section (GP3) to the moving speed (V_2) in the second section (GP2) to enter the second row R2.

As described above, the operation of the robot arm 100 may be more precisely controlled in the structure in which the laser is moved and irradiated by the robot arm equipped with the end-effector by maintaining the constant speed (or speed set to be changeable) for the motion pattern in the region of therapy (ROT) and varying the speed coinciding with the curved movement for the motion pattern outside the region of therapy (ROT).

The laser is irradiated to the first row (R1) and the second row (R2) forming the laser irradiation points and, as shown in FIG. 30, then the second section (GP2) and the third section (G3) of the guide path (GP) may be repeated and the irradiation of positions corresponding to all the laser irradiation points in the region of therapy (ROT) may be completed.

After the irradiation of the positions corresponding to all of the laser irradiation points is completed, the guide path (GP) may include the fourth section (GP4) for deviating from the region of therapy (ROT) to move at the end point Pt with a constant speed (V_4).

The moving speed (V_4) in the fourth section (GP4) of the guide path (GP) may be set equal to the moving speeds (V_1 and V_2) in the first section (GP1) and the second section (GP2).

Referring to FIGS. 29 and 30, the moving pattern is described under condition that the laser is irradiated while moving the laser unit of the robot arm 100 in both directions, that is, from left to right and from right to left. The present invention is not limited thereto, however, and the laser of the robot arm 100 may be irradiated while moving in one direction.

According to yet another embodiment of the present invention, in the third section (GP3) of the guide path (GP), it may be set to move along the curved path between two rows which are not adjacent to each other in the vertical direction among the plurality of rows forming the laser irradiation points.

Figure 31:
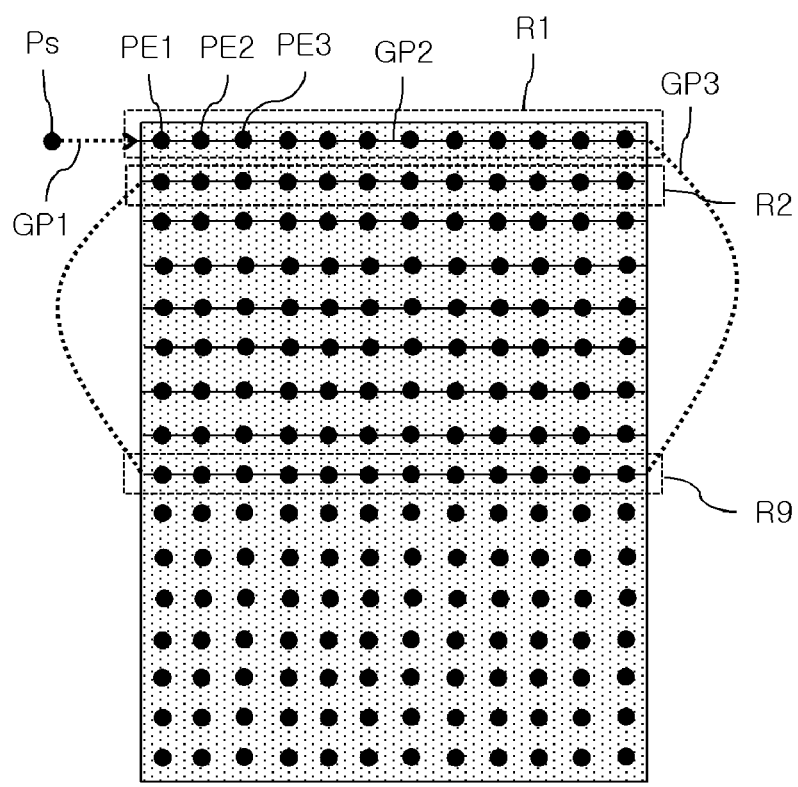

FIG. 31, in the third section (GP3) of the guide path (GP), the laser is moved along the curved path while changing the speed out from the first row R1 of the laser irradiation points, and the laser may enter the ninth raw R9 that is not immediately adjacent in the vertical direction.

Thereafter, the laser is sequentially irradiated on the laser irradiation points of the ninth row R9, and it is possible to enter the second row R2 on the upper side which is not just adjacent in the vertical direction by curving and moving from the ninth row R9 while varying the speed.

As described above, since the rows, spaced apart from each other with one or more rows, are moving in a curve section moving outside the region of therapy (ROT), it is possible to precisely control the operation of the robot arm 100 by increasing the distance of the curved movement section. Also, the laser is irradiated the laser irradiation points adjacent to each other in a short time, thereby preventing the deterioration of the skin.

Figure 32:
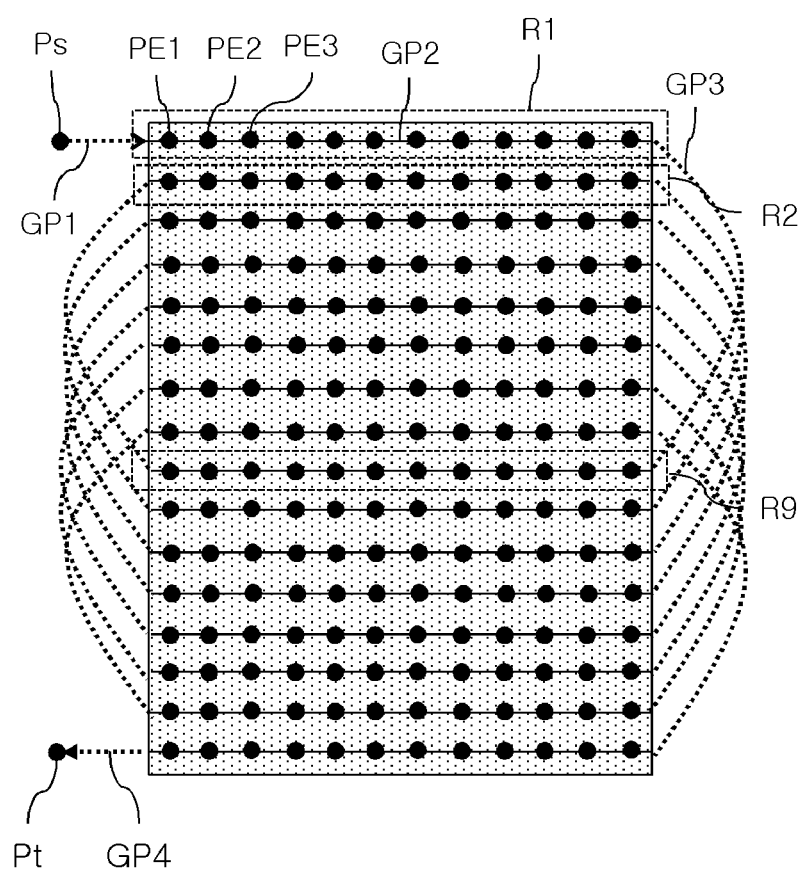

After the laser is irradiated on the first row R1, the ninth row R9 and the second row R2 forming the laser irradiation points, as shown in FIG. 32, the laser irradiation of positions corresponding to all the laser irradiation points in the region of therapy (ROT) may be completed by repeating the second section (GP2) and the third section (GP3) of the guide path (GP).

Although the present invention has been described with reference to FIGS. 29 to 32 as an example in which the laser is sequentially irradiated to the laser irradiation points adjacent to each other, the present invention is not limited to this, and the laser irradiation order for the laser irradiation points may be changed by considering the degree of pain, the variation of pupil, breath and pulse, sweating or the tension of muscle experienced by the patient.

According to another embodiment of the present invention, the laser may be irradiated by skipping one or more laser irradiation points among the plurality of laser irradiation points forming the same row in the region of therapy (ROT), and the laser unit of the robot arm 100 may be moved to a row on the previous guide path (GP) to irradiate the laser on the skipped laser irradiation point.

Figure 33:
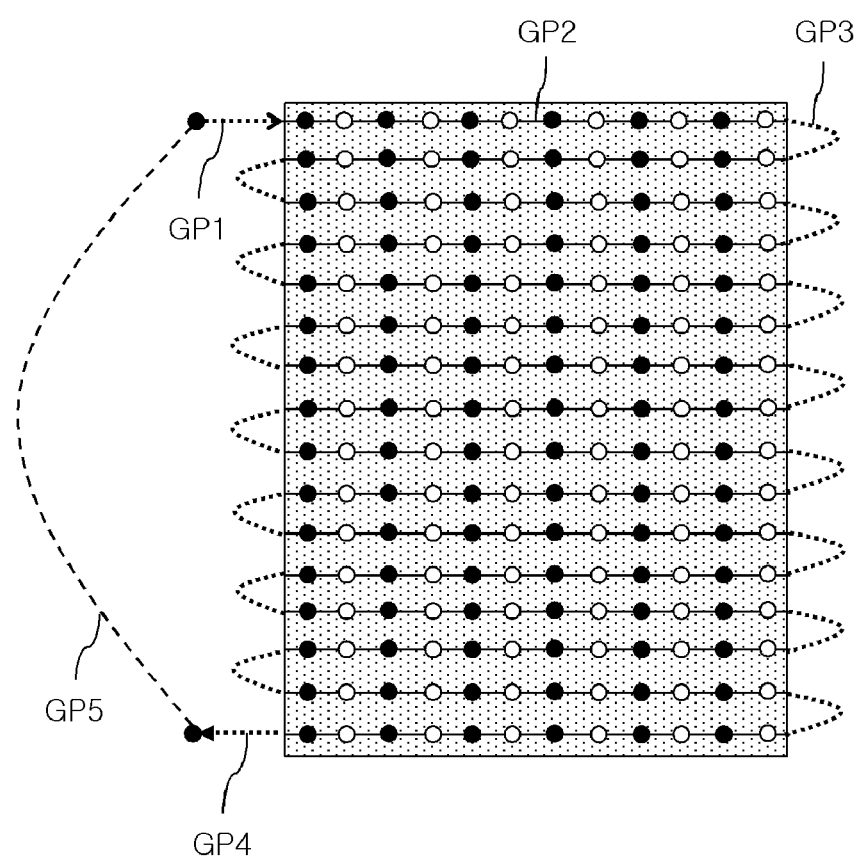
Figure 34:
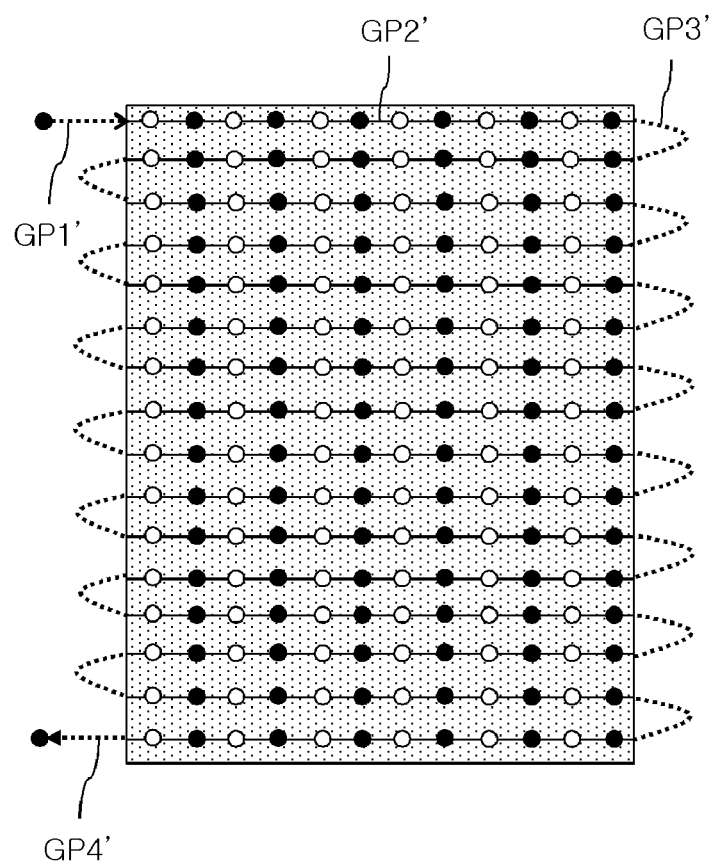

FIGS. 33 and 34 are shown for explaining another embodiment of the guide path in which the laser unit is moved, and it will be omitted the explanations of the guide path and the laser irradiation method which are the same as those described with reference to FIGS. 29 to 32.

Referring to FIG. 33, the guide path (GP) includes the first section (GP1) which moves from a starting point Ps to a fixed speed v_1 and enters the region of therapy (ROT), the second section (GP2) which irradiates the laser while linearly moving at a constant speed within the region of therapy (ROT), the third section (GP3) which moves along the curved path out from the region of therapy (ROT) and re-enters the region of therapy (ROT), the fourth section (GP4) which deviates from the region of therapy (ROT) to move at the end point Pt with a constant speed V_4, and the fifth section (GP5) for moving from the end point Pt to the start point Ps.

In the second section (GP2) of the guide path (GP), the laser may be sequentially irradiated by skipping one laser irradiation point among the plurality of laser irradiation points.

For this purpose, the speed of moving the laser unit of the robot arm may be faster than that described with reference to FIGS. 29 to 32, or the laser irradiation frequency may be lower than that described with reference to FIGS. 29 to 32 in the second section (GP2).

Also, the laser is moved along the curved path while varying the speed from the first row R1 of the laser irradiation points and entered to the second row R2 just adjacent in the vertical direction in the third section (GP3) of the guide path (GP).

After the laser is irradiated on the first row R1 and the second row R2 forming the laser irradiation points, the laser irradiation of some of the laser irradiation points in the (ROT) may be completed by repeating the second section (GP2) and the third section (GP3) of the guide path (GP).

After the laser irradiation is completed to the irradiation of the positions corresponding to all of the laser irradiation points, the guide path (GP) may include the fourth section for deviating from the region of therapy (ROT) to move at the end point Pt with a constant speed (V_4 (GP4).

Thereafter, the laser unit may be moved along the curved path to return from the end point Pt to the start point Ps in the fifth section (GP5) to irradiate the positions of the laser irradiation points in the region of therapy (ROT) where the laser is not irradiated.

After the laser unit of the robot arm is returned to the starting point Ps, the laser is irradiated on the laser irradiation points which are not irradiated with the laser along to the guide path (GP) as shown in FIG. 34, then the laser irradiation of all laser irradiation points may be completed.

The methods of controlling the guide path (GP) and the laser irradiation as described with reference to FIGS. 33 and 34, are for reducing the pain that the patient may feel as continuously irradiating to an adjacent position of the human surface. For example, it may be applied when "painless mode" is selected in the laser treatment apparatus according to the present invention.

In the above description as an example that the laser is irradiated although one of the laser irradiation points is skipped. However, two or more laser irradiation points may be skipped to be irradiated the laser, thereby further reducing the pain of the patient.

As shown in FIGS. 32 and 33, the laser may be irradiated while moving two times the entire region of therapy (ROT) of the patient's face. In addition, after the laser may be irradiated to two or more rows, the laser unit may be returned to the previous row to irradiate on the irradiation points where the laser is not irradiated.

The method of irradiating the laser by skipping one or more laser irradiation points may be applied separately from the application of the guide path (GP) which moves along the curved path outside the region of therapy (ROT).

As described above, it is determined the laser treatment conditions that whether to skip several laser irradiation points, to irradiate again the laser by returning to the previous position after the laser for several rows is irradiated, or to apply the guide path (GP) which moves along the curved path outside the region of therapy (ROT). The laser treatment conditions may be set according to various conditions such as the purpose of the treatment, the therapeutic effect, the treatment stage, and the degree of the pain felt by the patient.

However, the movement of the robot arm 100 may be set with the continuous motion pattern, even in such a case the movement of the robot arm 100, more specifically, the movement of the joints constituting the robot arm 100 may be discontinuous.

When the laser is irradiated at a position where the motion of the robot arm 100 is discontinuous, and the positions of the laser irradiation points previously set may be irregular since the position already irradiated may not be precisely controlled.

Thus, according to another embodiment of the present invention, the position of at least one of the plurality of laser irradiation points may be adjusted such that the laser is not irradiated at the position where the motion of the robot arm 100 is discontinuous.

Figure 35:
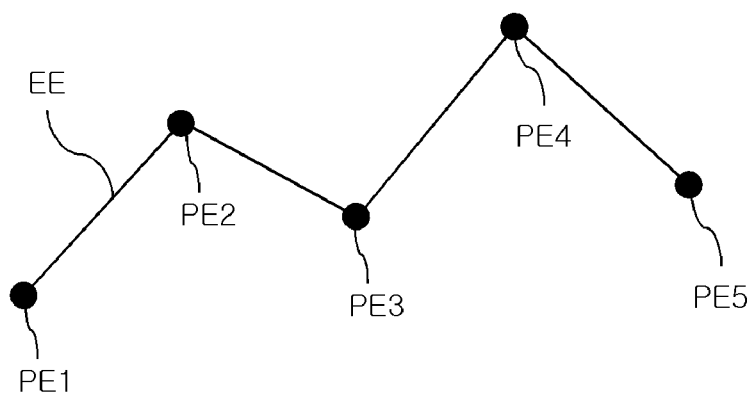
FIG. 35 is a view for explaining an embodiment of a method of adjusting the position of a laser irradiation point.
Figure 35:
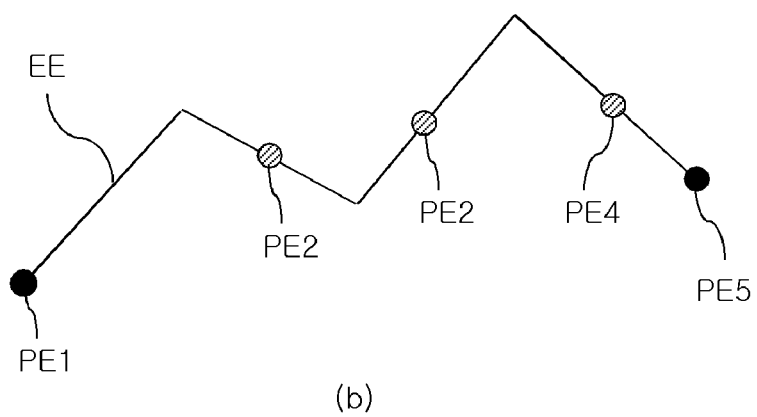

FIG. 35 is a diagram for explaining an embodiment of the method of adjusting the position of the laser irradiation point.

Referring to FIG. 35(a), the movement of the robot arm 100 (indicated by a solid line) may be discontinuous depending on an event, and the laser irradiation points (PE2, PE3, and PE4) may be set a position where the movement of the robot arm 100 may be discontinuous.

In this case, the positions of the laser irradiation points PE2, PE3, and PE4 may be adjusted to a position having continuous motion as shown in FIG. 35(b) so that the laser is not irradiated at the position where the motion of the robot arm 100 is discontinuous.

Although the embodiment of the present invention has been described with reference to the laser treatment apparatus using the robot arm, but the present invention is not limited thereto. In addition, it may be applicable to control movement patterns in various types of apparatus of a gantry type laser treatment apparatus for wrapping a patient's face or the laser treatment apparatus in the shape of a laser array patch attached to a patient's face.

Further, although the present invention is described as the example with reference to the laser treatment apparatus using the robot arm, the technical construction of the present invention may be applicable to a variety of energy based medical device, for treating the skin, using the high frequency, ultrasound, IPL (Intense Pulse Light), Psoralen-UV-A (PUVA), etc.

The methods according to the embodiments of the present invention may be made as a computer-executable program and stored in a computer-readable recording medium. Examples of the computer-readable recording medium include ROM, RAM, CD-ROM, a magnetic tape, a floppy disc, optical data storage devices, and it is implemented in the form of carrier waves (such as data transmission through the Internet).

Further, the computer-readable recording medium is distributed over network coupled computer systems so that the computer readable code is stored and executed in a distributed fashion. Then, the functional (functional) programs, codes, and code segments for accomplishing the present invention can be easily construed by programmers skilled in the art to which the invention pertains.

In this way, the above-described technical construction of the present invention it will be appreciated that without the person skilled in the art changing the technical spirit or essential features of the invention may be embodied in other specific forms.

Therefore, the embodiment described in the above examples should be understood as not be illustrative and not restrictive in all respects, and becomes the scope of the invention is indicated by the claims below rather than the foregoing description, the meaning and scope of the claims and all such modifications as derived from the equivalent concept be construed as being included in the scope of the invention.

What is claimed is:

1. A region division method for laser treatment of dividing an area of a subject to be treated by laser irradiation into a plurality of treatment regions, the method comprising:
   constructing a three-dimensional image of subject;
   using the three-dimensional image to obtain a normal vector for each of a plurality of points located on a surface of subject;
   dividing the plurality of points on the surface of the object subject into one or more groups based on a similarity between the obtained normal vectors; and
   generating a closed curve including at least some of the plurality of points grouped into a same group to set a treatment region.

2. The region division method for laser treatment of claim 1, wherein the dividing comprises grouping points having an angle between the normal vectors within a threshold range into one group.

3. The region division method for laser treatment of claim 2, wherein the threshold range is changed based on at least one of a treatment aim, a treatment time, a condition of the subject, and a user's setting.

4. The region division method for laser treatment of claim 2, wherein the dividing further comprises:
   setting any one of the plurality of points on the surface of the subject as a starting point;
   obtaining an angle between vertical vectors for the starting point and first peripheral points located around the starting point; and
   if the angle thus obtained is equal to or less than the threshold range,
   grouping the starting point and the first peripheral points into a first group.

5. The region division method for laser treatment of claim 4, wherein the dividing further comprises:
   setting any one of remaining points which are not grouped into the first group as a reference point;
   obtaining an angle between vertical vectors for the reference point and second peripheral points located around the reference point and not included in the first group; and
   if the angle thus obtained is equal to or less than the threshold range,
   grouping the reference point and the second peripheral points into a second group.

6. The region division method for laser treatment of claim 4, wherein the starting point is randomly selected or designated by a user from the plurality of points on the surface of the subject, or alternatively designated to correspond to a particular site on a face recognized using the 3D image of the subject.

7. The region division method for laser treatment of claim 1, further comprising setting a minimum number of points to be grouped into one group.

8. A laser treatment method of dividing an area of a subject to be treated by laser irradiation into a plurality of treatment regions, the method comprising:
constructing a three-dimensional image of the subject;
using the three-dimensional image to obtain a normal vector for each of a plurality of points located on a surface of the subject;
dividing the plurality of points on the surface of the subject into one or more groups based on a similarity between the obtained normal vectors;
generating a closed curve including at least some of the plurality of points grouped into a same group to set a treatment region;
setting a guide path which passes through the treatment region;
setting a plurality of laser irradiation points arranged on the guide path; and
sequentially irradiating a laser to a position corresponding to each of the plurality of laser irradiation points on the surface of the subject.

9. The laser treatment method of claim 8, wherein the dividing comprises grouping points having an angle between the normal vectors within a threshold range into one group.

10. The laser treatment method of claim 8, further comprising selecting the treatment region in which the guide path is set from the divided plurality of treatment regions by a user.

11. The laser treatment method of claim 8, further comprising determining an order of treatment for the divided plurality of treatment regions.

12. The laser treatment method of claim 11, wherein the order of treatment is determined to be non-continuous for adjacent regions among the plurality of treatment regions.

13. The laser treatment method of claim 8, wherein the guide path comprises a first section from which the laser enters the treatment region, a second section in which the laser moves at a constant speed within the treatment region, and a third section from which the laser re-enters the treatment region by moving along a curved path while varying the speed outside the treatment region, and wherein the laser is irradiated at a constant frequency in the second section.

14. The laser treatment method of claim 8, wherein the laser is irradiated by a robot arm with an end effector, and wherein the laser is irradiated at a constant angle from the end effector while treatment is performed for one divided treatment region.

15. An apparatus for treatment of dividing an area of a subject to be treated by laser irradiation into a plurality of treatment regions, the apparatus comprising:
a vision controlling unit for constructing a three-dimensional image of the subject, and for setting a treatment region irradiated by a laser on a surface of the subject, a guide path passing through the treatment region, and laser irradiation points arranged on the guide path;
a laser unit for sequentially irradiating the laser to a position corresponding to the laser irradiation points in the surface of the subject; and
a motion controlling unit for controlling movement of the laser unit and the laser irradiation based on the set guide path and the laser irradiation points,
wherein the vision controlling unit is configured to use the three-dimensional image to obtain a normal vector for each of a plurality of points located on the surface of the subject; divide the plurality of points on the surface of the subject into one or more groups based on a similarity between the obtained normal vectors; and generate a closed curve including at least some of the plurality of points grouped into a same group to set the treatment region.

16. The laser treatment apparatus of claim 15, wherein the vision controlling unit is further configured to group points having an angle between the normal vectors within a threshold range into one group with respect to the plurality of points on the surface of the subject.

17. The laser treatment apparatus of claim 15, wherein the vision controlling unit is further configured to determine an order of treatment for the divided plurality of treatment regions and the order of treatment is determined to be non-continuous for adjacent regions among the plurality of treatment regions.

18. The laser treatment apparatus of claim 15, wherein the guide path comprises a first section from which the laser enters the treatment region, a second section in which the laser moves at a constant speed within the treatment region, and a third section from which the laser re-enters the treatment region by moving along a curved path while varying the speed outside the treatment region, and wherein the laser is irradiated at a constant frequency in the second section.

19. The laser treatment apparatus of claim 15, wherein the laser unit comprises a robot arm with an end effector, and wherein the laser is irradiated at a constant angle from the end effector while treatment is performed for one divided treatment region.

* * * * *